United States Patent
Aufdermarsh et al.

(10) Patent No.: US 7,521,510 B2
(45) Date of Patent: Apr. 21, 2009

(54) BISAMINOPHENYL-BASED CURATIVES AND AMIDINE-BASED CURATIVES AND CURE ACCELERATORS FOR PERFLUOROELASTOMERIC COMPOSITIONS

(75) Inventors: Carl A. Aufdermarsh, Asheville, NC (US); Harshad P. Amin, New Braunfels, TX (US); Anestis Logothetis, Wilmington, DE (US)

(73) Assignee: Greene, Tweed of Delaware, Inc, Wilmington, DE (US)

( * ) Notice: Subject to any disclaimer, the term of this patent is extended or adjusted under 35 U.S.C. 154(b) by 0 days.

(21) Appl. No.: 11/436,108

(22) Filed: May 17, 2006

(65) Prior Publication Data

US 2007/0027260 A1 Feb. 1, 2007

Related U.S. Application Data

(63) Continuation of application No. 10/768,838, filed on Jan. 29, 2004, now abandoned.

(60) Provisional application No. 60/443,718, filed on Jan. 29, 2003.

(51) Int. Cl.
*C08F 259/08* (2006.01)
*C08F 14/18* (2006.01)

(52) U.S. Cl. .................... 525/276; 525/259; 525/326.2; 525/326.3

(58) Field of Classification Search ................. 525/259, 525/276, 326.2, 326.3
See application file for complete search history.

(56) References Cited

U.S. PATENT DOCUMENTS

| | | |
|---|---|---|
| 2,676,985 A | 4/1954 | Husted |
| 3,317,484 A | 5/1967 | Fritz et al. |
| 3,347,901 A | 10/1967 | Fritz et al. |
| 3,669,941 A | 6/1972 | Dorfman et al. |
| 3,845,051 A | 10/1974 | Zollinger |
| 4,138,426 A | 2/1979 | England |
| 4,141,874 A | 2/1979 | Oka et al. |
| 4,242,498 A | 12/1980 | Rosser et al. |
| 4,281,092 A | 7/1981 | Breazeale |
| 4,394,489 A | 7/1983 | Aufdermarsh |
| 4,413,094 A | 11/1983 | Aufdermarsh |
| 4,434,106 A | 2/1984 | Rosser et al. |
| 4,487,903 A | 12/1984 | Tatemoto et al. |
| 4,496,682 A | 1/1985 | Schmiegel |
| 4,525,539 A | 6/1985 | Feiring |
| 4,922,019 A | 5/1990 | Lau et al. |
| 4,983,680 A | 1/1991 | Ojakaar |
| 4,983,697 A | 1/1991 | Logothetis |
| 5,001,278 A | 3/1991 | Oka et al. |
| 5,028,728 A | 7/1991 | Schneider et al. |
| 5,266,650 A | 11/1993 | Guerra et al. |
| 5,319,025 A | 6/1994 | Weigelt |
| 5,447,993 A | 9/1995 | Logothetis |
| 5,565,512 A | 10/1996 | Saito et al. |
| 5,621,145 A | 4/1997 | Saito et al. |
| 5,637,648 A | 6/1997 | Saito et al. |
| 5,668,221 A | 9/1997 | Saito et al. |
| 5,672,758 A | 9/1997 | Sonoi et al. |
| 5,677,389 A | 10/1997 | Logothetis et al. |
| 5,688,872 A | 11/1997 | Sonoi et al. |
| 5,693,748 A | 12/1997 | Ikeda et al. |
| 5,696,189 A | 12/1997 | Legare |
| 5,700,879 A | 12/1997 | Yamamoto et al. |
| 5,767,204 A | 6/1998 | Iwa et al. |
| 5,789,489 A | 8/1998 | Coughlin et al. |
| 5,789,509 A | 8/1998 | Schmiegel |
| 5,877,264 A | 3/1999 | Logothetis et al. |
| 5,891,941 A | 4/1999 | Tanaka et al. |
| 6,114,452 A | 9/2000 | Schmiegel |
| 6,211,319 B1 | 4/2001 | Schmiegel et al. |
| 6,221,971 B1 | 4/2001 | Tabb |
| 6,281,296 B1 | 8/2001 | MacLachlan et al. |
| 6,429,271 B1 | 8/2002 | Schmiegel |
| 6,638,999 B2 | 10/2003 | Bish et al. |
| 6,657,013 B2 | 12/2003 | Grootaert et al. |
| 6,730,760 B2 | 5/2004 | Grootaert et al. |
| 6,737,479 B2 | 5/2004 | Faulkner |

(Continued)

FOREIGN PATENT DOCUMENTS

| | | |
|---|---|---|
| EP | 0 708 140 A1 | 4/1996 |
| EP | 0 708 140 B1 | 8/1998 |
| RU | 606867 | 5/1978 |
| WO | WO 00/08076 | 2/2000 |
| WO | WO 00/09603 A1 | 2/2000 |
| WO | WO 01/59005 A2 | 8/2001 |
| WO | WO 02/060969 A1 | 8/2002 |
| WO | WO 2004/033546 A1 | 4/2004 |

OTHER PUBLICATIONS

Arcella, et al., "New Peroxide Curable Perfluoroelastomer for High Temperature Applications", Paper No. 16, *ACS Rubber Division Meeting*, Indianapolis, IN (2 pages)(May 5-8, 1998).

(Continued)

*Primary Examiner*—Ling-Siu Choi
(74) *Attorney, Agent, or Firm*—Flaster/Greenberg P.C.

(57) ABSTRACT

Novel monoamidine, monoamidoxime and bisamidine curatives, co-curatives and cure accelerators are provided for use with perfluoroelastomeric compositions as well as novel synthesis methods for making monoamidine- and monoamidoxime-based curatives, co-curatives and cure accelerators. Also provided are diphenyl-based curatives, co-curatives and cure accelerators having sufficiently high molecular weight such that the melting temperature of the curatives, co-curatives and cure accelerators is no greater than about 240° C., and more preferably no greater than about 230° C.

20 Claims, No Drawings

U.S. PATENT DOCUMENTS

| | | | |
|---|---|---|---|
| 6,750,304 | B2 | 6/2004 | Kaspar et al. |
| 6,846,880 | B2 * | 1/2005 | Grootaert et al. ............. 525/259 |
| 2002/0026014 | A1 * | 2/2002 | Bish et al. ................... 525/375 |
| 2002/0183458 | A1 | 12/2002 | Grootaert et al. |
| 2004/0024133 | A1 | 2/2004 | Hetherington |
| 2004/0024134 | A1 | 2/2004 | Grootaert et al. |
| 2004/0044139 | A1 | 3/2004 | Grootaert et al. |
| 2004/0048983 | A1 | 3/2004 | Hochgesang et al. |
| 2005/0143529 | A1 | 6/2005 | Grootaert et al. |

OTHER PUBLICATIONS

Brown, *Abstracts of the 128th National Meeting of the American Chemical Society*, Minneapolis, MN (Sep. 1955); the *134th National Meeting of the ACS*, Chicago, III. (Sep. 1958); and the *147th National Meeting of the ACS*, Philadelphia, PA (5 pages) (Apr. 1964).

Brown et al., "Reactions of the Perfluoroalkylnitriles. IV. Preparation and Characterization of Some N'-(Perfluoroacylimidoyl)perfluoroakylamidines and Their Metal Chelates," *J. Org. Chem.*, vol. 28, pp. 1122-1127 (1963).

Brown, "Thermally Stable Polymers from Condensation Polymerization of Perfluoroalkylamidines," *J. Polymer Sci.*, vol. 44, pp. 9-22 (1960).

Grindahl et al., "The Preparation and Coupling of Some α-Haloperfluoromethyl-s-triazines," *J. Org. Chem.*, 32, pp. 603-607 (1967).

Hertz, Jr., "11. Temperature Resistant Elastomers- D. Fluoroelastomers." *Basic Elastomer Technology, ACS Rubber Division* (2001).

Korus, "High Performance Perfluoroalkyl Ether Triazine Elastomers", *Ind. Eng. Chem. Prod. Res. Dev.* 20(4), pp. 694-696 (1981).

Reilly et al., Reactions of the Perfluoronitriles. II. Syntheses of 2,4,6-*tris*(Perfluoroalkyl)-1,3,5-Triazines[1,2], *J. Org. Chem.*, vol. 22, pp. 698 (1957).

Reilly et al., "Reactions of Perfluoronitriles. I. Synthesis of Derivatives of Perfluoroamidines, N-Substituted Perfluoroamidines and Perfluorothioamides," *J. Amer. Chem. Soc.*, vol. 78, pp. 6032-6034 (1956).

Smith, *The Chemistry of Open-Chain Organic Nitrogen Compounds*, vol. 1, pp. 178-179 (1965).

Dorfman et al., "A Synthesis of Poly(2,4-Perfluoroalkylene-6-Perfluoroalkyltriazine)s", *89th National Meeting of the Division of Rubber Chemistry of the American Chemical Society*, San Francisco, CA (Spring 1966).

Evers, "Low Glass Transition Temperature Fluorocarbon Ether Bibenzoxazole Polymers," *J. Poly. Sci.*, vol. 16, pp. 2833-2848 (1978).

* cited by examiner

BISAMINOPHENYL-BASED CURATIVES AND AMIDINE-BASED CURATIVES AND CURE ACCELERATORS FOR PERFLUOROELASTOMERIC COMPOSITIONS

CROSS-REFERENCE TO RELATED APPLICATIONS

This application claims the benefit under 35 U.S.C. 119(e) of U.S. Provisional Application No. 60/443,718, filed Jan. 29, 2003.

BACKGROUND OF THE INVENTION

Fluoroelastomers, and more particularly, perfluoroelastomers are materials known for their high levels of chemical resistance, plasma resistance, acceptable compression set resistance and satisfactory mechanical properties. Fluoroelastomers have thus found use as seals, gaskets and linings. When high temperature or aggressive or harsh environments, such as corrosive fluids, solvents, lubricants, and oxidizing or reducing conditions are implicated, perfluoroelastomers are the materials of choice. Fluoroelastomers are made by various routes using fluorinated monomers. Perfluoroelastomers are typically formed by using perfluorinated monomers, including a perfluorinated curesite monomer, polymerizing the monomers and curing (cross-linking) the composition using a curing agent which reacts with the incorporated curesite monomer to form a material which exhibits elastomeric properties. Suitable curesite monomers include, among others, those having cyano curesites. Examples of primary and secondary cyano-containing curesite monomers are known in the art. It is believed that in curesite monomers having cyano curesites, certain curing agents trimerize the cyano cure sites which join to form triazines.

Known curing agents include organometallic compounds and the hydroxides thereof, especially organotin compounds, including allyl-, propargyl-, triphenyl- and allenyl tin and the hydroxides. The tetraalkyltin compounds or tetraaryltin compounds, for example tetraphenyltin, are common. However, these curing agents provide a relatively slow rate of cure, are toxic and can introduce metallic contaminants to resulting elastomers.

Curing agents containing amino groups have also been employed. Bisaminophenols, bisaminothiophenols and bisamidrazones are additional types of curing agents. Those having a diphenyl structure having substitutions on each phenyl ring of amino and hydroxyl, diamine, and amino and thio are generally known in the art as being connected by structures including: —$SO_2$—, —O—, —CO—, alkyl groups of 1-6 carbon atoms, and a carbon-carbon double bond. While perfluoroalkyl groups of 1-10 carbon atoms have been loosely described, actual synthesis and use of such compounds as curatives have not been demonstrated. Those diphenyl structure type materials which are in use and have known syntheses, are primarily compounds which have three carbon alkyl groups and in which the phenyl groups are attached to the central (second) carbon in the bis-position. For example, the most well known curative of this type is 2,2-bis[3-amino-4-hydroxyphenyl]hexafluoropropane, also known as diaminobisphenol AF or BOAP.

BOAP is a crystalline solid with a melting point of about 245-248° C. BOAP is not very compatible with perfluoroelastomers, is difficult to disperse rapidly and uniformly with perfluoroelastomers, and is thus a relatively slow-acting curative.

R. C. Evers, J. Polym. Sci. 16, 2833-2848 (1978) describe use of fluorocarbon ether bisaminophenols as monomers for making fluorocarbon ether-bibenzoxazole polymers. Evers outlined a synthesis route for the fluorocarbon ether bisaminophenols with α, ω-diiodofluorocarbon ethers as intermediates. U.S. Pat. No. 2,676,985 of Husted, Reilly & Brown in JACS 78:6032 (1956), Grigas and Taurins, Can. J. Chem., vol. 39, 414-419 (1961) and Grigas and A. Taurins, Can. J. Chem., vol. 39, 761-764 (1961) describe previously known synthesis routes for formation of amidines.

With respect to ways to speed up slow curing agents, such as BOAP, there are also traditional accelerators used in the art including organic or inorganic ammonium salts, e.g. perfluorooctanoate, ammonium perfluoroacetate, ammonium thiocyanate, and ammonium sulfamate; urea; t-butyl carbamate; acetaldehyde ammonia; tetraalkylphosphonium salts, tetraalkylammonium salts, and trialkylsulfonium salts, such as benzyltriphenylphosphonium chloride, benzyltriphenylphosphonium bromide, benzyltriphenylphosphonium phenolate of bisphenol AF, tetrabutylammonium hydrogen sulfate, and tetrabutylammonium bromide. However, such compounds tend to have side reactions that can result in undesirable byproducts.

Accordingly, there remains a need in the art for an improved curing agent capable of more easily dispersing in and more quickly curing perfluoroelastomers, particularly cyano curable perfluoroelastomers. There is further a need in the art for a cure accelerator for perfluoroelastomer curatives which accelerate the cure rate of and maintain the beneficial properties of perfluoroelastomers.

BRIEF SUMMARY OF THE INVENTION

The invention includes monoamidine-based and monoamidoxime-based curatives, co-curatives and cure accelerators for perfluoroelastomeric compositions. The invention further includes such materials as curatives having the general formula (I):

wherein Y is selected from the group consisting of substituted alkyl, alkoxy, aryl, aralkyl or aralkoxy groups of from 1 to about 22 carbon atoms; substituted or unsubstituted halogenated alkyl, alkoxy, aryl, aralkyl or aralkoxy groups of from about 1 to about 22 carbon atoms, and perfluoroalkyl, perfluoroalkoxy, perfluoroaryl, perfluoroaralkyl or perfluoroaralkoxy groups of from 1 to about 22 carbon atoms; and $R^1$ is hydrogen; substituted or unsubstituted lower alkyl or alkoxy groups of from 1 to about 6 carbon atoms; and an amino group; and $R^2$ is $R^1$ or hydroxyl.

The invention also includes bisamidine-based curatives, co-curatives and cure accelerators for perfluoroelastomeric compositions. The invention further includes such compounds as represented by formula (II):

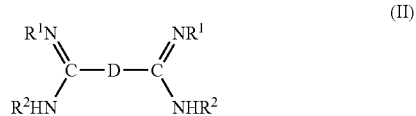

wherein D is selected from the group consisting of unsubstituted or substituted halogenated alkyl, alkoxy, aryl, aralkyl or aralkoxy groups having from about 1 to about 22 carbon atoms; and perfluoroalkyl, perfluoroalkoxy, perfluoroaryl, perfluoroaralkyl or perfluoroalkoxy groups of from 1 to about 22 carbon atoms; and $R^1$ and $R^2$ are each independently selected to be hydrogen; substituted or unsubstituted lower alkyl or alkoxy groups of from 1 to about 6 carbon atoms and an amino group.

The invention includes a curable perfluoroelastomeric composition, comprising: (a) a perfluoropolymer having at least one curesite monomer comprising a cyano functional group; and (b) at least one monoamidine-based or monoamidoxime-based curative.

A curable perfluoroelastomeric composition is also within the invention which comprises (a) a perfluoropolymer having at least one curesite monomer comprising a cyano functional group; (b) a functionalized diphenyl-based curative; and (c) a cure accelerator selected from the group consisting of at least one monoamidine-based cure accelerator, at least one monoamidoxime-based cure accelerator, at least one bisamidine-based cure accelerator and combinations thereof. Preferred curable perfluoroelastomeric compositions are also included in the invention in which the functionalized diphenyl-based curative has formula (III):

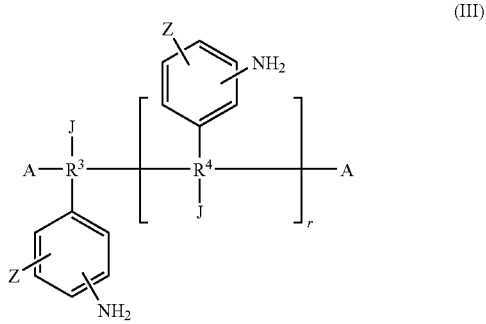

(III)

wherein r is 0 or 1;

$R^3$ and $R^4$ are each independently selected from the group consisting of a carbon atom;

substituted and unsubstituted and branched and straight chain carbon groups of from about 2 to about 22 carbon atoms selected from the group consisting of alkyl groups, halogenated alkyl groups, and perfluorinated alkyl groups, each of which groups may be interrupted by at least one oxygen atom;

each Z is independently selected from the group consisting of an amino, mercapto, sulfhydryl, or hydroxyl group;

each J is independently selected to be formula (IV):

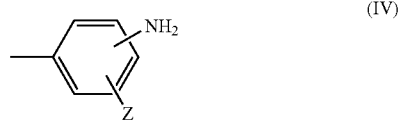

(IV)

or A; and each A is independently selected from the group consisting of formula (IV); a fluorine atom;

and unsubstituted and substituted and branched and straight chain carbon-based groups which are selected from group consisting of alkyl, halogenated alkyl, and perfluoroalkyl groups of from 1 to about 22 carbon atoms; each of which groups may be interrupted by at least one oxygen atom;

wherein when r is 0 and $R^3$ is a carbon atom, at least one of J and each A is not formula (IV).

The invention further includes a curative for a perfluoroelastomeric composition, in which the curative has formula (III) as noted above.

The invention includes a curative for a perfluoroelastomeric composition, comprising a functionalized diphenyl-based curative which has a sufficiently high molecular weight so that the melting point is no greater than about 240° C., and in certain preferred embodiments is no greater than about 230° C.

A method for using a compound having formula (I) below is also included in the invention:

(I)

wherein Y is selected from the group consisting of substituted alkyl, alkoxy, aryl, aralkyl or aralkoxy groups of from 1 to about 22 carbon atoms; substituted or unsubstituted halogenated alkyl, alkoxy, aryl, aralkyl or aralkoxy groups of from about 1 to about 22 carbon atoms, and perfluoroalkyl, perfluoroalkoxy, perfluoroaryl, perfluoroaralkyl or perfluoroaralkoxy groups of from 1 to about 22 carbon atoms; and $R^1$ is hydrogen; substituted or unsubstituted lower alkyl or alkoxy groups of from 1 to about 6 carbon atoms; and an amino group; and $R^2$ is $R^1$ or hydroxyl, and wherein the compound is used as a curative for a perfluoroelastomeric composition.

A method for curing a perfluoroelastomeric composition is also included which comprises using a mixture of (i) at least one compound selected from the group consisting of monoamidine-based compounds, monoamidoxime-based compounds, and mixtures thereof and (ii) at least one bisamidine-based compound as co-curatives for the perfluoroelastomeric composition.

A method for accelerating curing of a perfluoroelastomeric composition is within the invention which method comprises using a cure accelerator for a curative, wherein the cure accelerator is selected from the group consisting of a monoamidine-based compound, a monoamidoxime-based compound, a bisamidine-based compound and combinations thereof.

The invention also includes a method for curing a perfluoroelastomeric composition comprising using a functionalized diphenyl-based curative having a sufficiently high molecular weight such that the melting point is no greater than about 240° C. as a curative for the perfluoroelastomeric composition, and in certain preferred embodiments is the melting point is no greater than about 230° C.

Also included within the invention is a method for making a curative. The method comprises (a) reacting an organic alkylacid with an alcohol to form an alkylester; (b) reacting the alkyl ester with ammonia to form an alkylcarboxyamide; (c) reacting the alkylcarboxyamide with a dehydrating agent to form an alkyl nitrile; and (d) reacting the alkyl nitrile with at least one of ammonia or an amine to form a curative, wherein the curative is capable of curing or accelerating the cure of a perfluoroelastomeric composition.

In addition to the above method, the invention includes a method for making a bisaminophenol-based curative. That method comprises: (a) reacting an perfluoroacyl fluoride with potassium fluoride to form a potassium alcoholate reaction product; (b) reacting the potassium alcoholate reaction product with a perfluoroallylfluorosulfate to form a perfluoroallyl ether; (c) reacting the perfluoroallyl ether with an oxidizing agent to form a perfluoroglycidyl ether; (d) reacting the perfluoroglycidyl ether with aluminum chloride in a fluorinated solvent to isomerize an epoxide group on the perfluoroglyicdyl ether to a ketone; (e) reacting the ketone group with phenol in the presence of hydrogen fluoride to form a bisphenol-based compound; (f) nitration of the bisphenol-based compound to give a bisnitrophenol-based compound; and (g) reduction of the bisnitrophenol-based compound to form a bisaminophenol curative, wherein the bisaminophenol-based curative is capable of curing a perfluoroelastomeric composition.

A substituted bisaminophenyl-based curative for perfluoroelastomers having cyano-group containing curesite monomers is included within the invention. The bisaminophenyl-based curative is a substituted bisaminophenyl-based curative which has formula (IIIa):

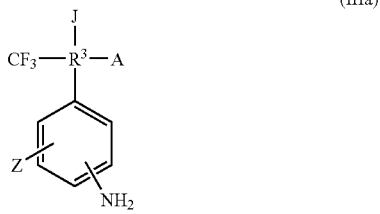

(IIIa)

wherein $R^3$ is a carbon atom; Z is an amino, sulfhydryl, or hydroxyl group; J is formula (IV):

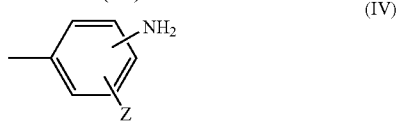

(IV)

and A is selected from the group consisting of unsubstituted and substituted and branched and straight chain carbon-based groups, wherein the carbon-based groups are selected from the group consisting of perfluoroalkyl and perfluoroalkoxy groups of from 1 to about 22 carbon atoms.

The invention further includes a perfluoroelastomeric composition comprising a bisaminophenyl-based curative for perfluoroelastomers having cyano-group containing curesite monomers, wherein the curative is a substituted bisaminophenyl-based curative which has formula (III):

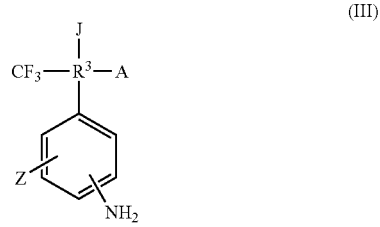

(III)

wherein $R^3$ is a carbon atom; Z is an amino, sulfhydryl, or hydroxyl group; J is formula (IV):

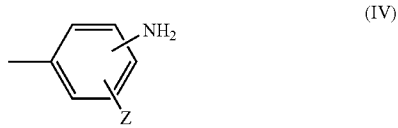

(IV)

and A is selected from the group consisting of unsubstituted and substituted and branched and straight chain carbon-based groups, wherein the carbon-based groups are selected from the group consisting of perfluoroalkyl and perfluoroalkoxy groups of from 1 to about 22 carbon atoms.

DETAILED DESCRIPTION OF THE INVENTION

The present invention is directed to low melting diphenyl-based, preferably diaminophenyl-based and more preferably perfluorinated diaminophenyl-based curatives and co-curatives for perfluoroelastomeric compositions and novel methods of synthesis of preferred functionalized diphenyl-based curing agents. The invention is further directed to amidine-based cure accelerators, curatives and co-curatives for perfluoroelastomers. The curing agents and co-curing agents of the invention show improved mixing with perfluoroelastomeric compositions and the curatives, co-curatives and accelerators further demonstrate faster cure rates compared with conventional curing agents such as BOAP. Additionally, the amidine-based curatives and accelerators provide faster cures.

As used herein, a perfluoroelastomer may be any cured elastomeric material, derived by curing a perfluoroelastomeric composition (as defined herein) which includes a curable perfluoropolymer having a functional group to permit cure. A perfluoroelastomer is substantially completely fluorinated with respect to the carbon atoms of the perfluoropolymer. By this it is meant that as would be understood, based on this disclosure, that some residual hydrogen may exist in the functional crosslinking group in some perfluoroelastomeric compositions according to the present disclosure. The perfluoropolymers, used in perfluoroelastomeric compositions to form perfluoroelastomers upon cure, are formed by polymerizing one or more perfluorinated monomers, one of which preferably has a perfluorinated curesite monomer having a functional group to permit curing.

As used herein, a perfluoroelastomeric composition is a polymeric composition including a curable perfluoropolymer. The perfluoropolymer as noted above is formed by polymerizing two or more perfluorinated monomers, plus at least one perfluorinated monomer which has at least one functional group to permit curing, i.e. at least one perfluoropolymeric curesite monomer. Such materials are also referred to general as FFKMs (perfluoroelastomers) in accordance with the American Society for Testing and Materials (ASTM) definition (ASTM-D-1418-01a), incorporated herein fully by reference and are also described further herein. The definition provides that a perfluoroelastomer is a perfluorinated rubber of the polymethylene type having all fluoro, perfluoroalkyl, or perfluoroalkoxy substitutent groups on the polymer chain; a small fraction of these groups may contain functionality to facilitate vulcanization. The perfluoroelastomer composition may include any suitable curable perfluoropolymer(s) (FFKM) capable of being cured to form a perfluoroelastomer, and one or more curing agents as described herein.

Such perfluoroelastomeric compositions may preferably include two or more of various perfluorinated copolymers of at least one fluorine-containing ethylenically unsaturated monomer, such as tetrafluoroethylene (TFE); a perfluorinated olefin, such as hexafluoropropylene (HFP); and a perfluoroalkylvinyl ether (PAVE) which include alkyl groups that are straight or branched and which include one or more ether linkages, such as perfluoro(methyl vinyl ether), perfluoro (ethyl vinyl ether), perfluoro(propyl vinyl ether) and similar compounds. Examples of preferred PAVES include those described in U.S. Pat. No. 5,001,278 and in WO 00/08076, incorporated herein by reference. Other suitable PAVEs are described, for example, in U.S. Pat. Nos. 5,696,189 and 4,983,697, also incorporated herein by reference.

Preferred perfluoropolymers are terpolymers or tetrapolymers of TFE, PAVE, and at least one perfluorinated cure site monomer which incorporates a functional group to permit crosslinking of the terpolymer, at least one of which is a curesite capable of being cured by the curatives and co-curatives of the invention. In one embodiment, the curesite monomer(s) provide curesites which may be cured with either the inventive curative or inventive co-curatives or by other curatives not within the scope of the invention, but which are capable of having an accelerated cure when acted on by the cure accelerators of the present invention.

Most preferred curesite monomers include those having cyano curesites, regardless of the location of the cyano group, e.g., primary and secondary cyano group curesite monomers. Examples of cyano curesite monomers are described in detail herein, and may be found in, for example, U.S. Pat. No. 4,281,092. Such cyano group containing cure site monomers are well known in the art. Combinations of one or more of these curesite monomers with each other or with other well known curesite monomers may also be used within the scope of the invention.

Useful cyano cure site monomers include fluorinated olefins and fluorinated vinyl ethers, each having a cyano group of which the following are general examples:

$CF_2$=CF—O—$[CF_2]_n$—CN, wherein n is from about 2 to about 12, and preferably about 2 to about 6;

$CF_2$=CF—O—$[CF_2$—$CF(CF_3)$—O$]_n$—$CF_2$—CF$(CF_3)$—CN, wherein n is from 0 to about 4, preferably from 0 to about 2;

$CF_2$=CF—$[OCF_2CF(CF_3)]_m$—O—$[CF_2]_n$—CN, wherein m is from about 1 to about 2, and n is from about 1 to about 4; and $CF_2$=CF—$[CF_2]_n$—O—$CF(CF_3)$—CN, wherein n is from 2 to about 4.

Specific examples include primary curesite monomers such as $CF_2$=CFOCF$_2$CF(CF$_3$)OCF2CF2CN (referred to generally as 8-CNVE) and secondary curesite monomers such as $CF_2$=CF—O[CF$_2$]$_3$—O—CF[CF$_3$]—CN. Such curesite monomers may be used alone or in combination. Especially preferred is a combination of curesite monomers as shown below in a fluoropolymeric or perfluoropolymeric chain as follows:

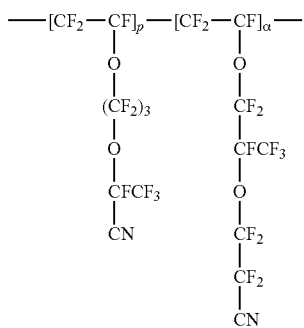

wherein p represents a secondary curesite monomer present in a fluoropolymer or perfluoropolymers in an amount from about 0.1 to about 12 mol %, preferably about 1 to about 4 mol %, and α represents a primary curesite monomer present in an amount from about 0.1 to about 12 mol % and preferably from about 1 to about 7 mol %. It is preferred that the molar ratio of the primary curesite monomer to the secondary curesite monomer in the copolymer is from about 1:1 to about 10:1, preferably 9:1.

It will be understood based on this disclosure that additional types of cure site monomers which contain cyano groups as curesites and those which do not contain cyano groups may be used in addition to or, in certain cases, in place of the preferred curesite monomers noted above, provided that the curesite monomers are capable of being cured by the preferred curatives and co-curatives and/or capable of experiencing an accelerated curing reaction when using the cure accelerators of the invention as described herein. Common examples of other types of curesite monomers include olefins, including partially or fully halogenated olefins, such as ethylene, vinylidene fluoride, vinyl fluoride, trifluoroethylene, bromotetrafluorobutene, bromotrifluoroethylene, 1-hydropentafluoropropene and 2-hydropentafluoropropene. Such additional cure site monomer(s) may be present in ranges as noted above and are preferably are generally present in amounts of about 0.1 to about 5 mole percent, more preferably about 0.1 to about 2.5 mole percent, and most preferably about 0.3 to about 1.5 mole percent.

Other additives, such as co-curatives, curing agents or accelerators, other than those of the present invention; processing aids; fillers and the like may also be included as optional components of the perfluoroelastomeric compositions of the invention. Such additives include fillers such as graphite, carbon black, clay, silicon dioxide, fluoropolymeric particulates (for example, TFE homopolymer and copolymer micropowders), barium sulfate, silica, titanium dioxide, acid acceptors, cure accelerators, glass fibers, or polyaramid fibers such as Keviar, other curing agents and/or plasticizers or other additives known or to be developed in the fluoroelastomeric art and perfluoroelastomeric art. Preferred perfluoropolymers/perfluoroelastomers include Simriz®, available from Freudenberg of Germany, Dyneon®, available from Minnesota Mining & Manufacturing in Minnesota, Daiel-Perfluor®, available from Daikin Industries, Ltd. of Osaka, Japan. Similar materials are also available from Ausimont S.p.A. in Italy and from Federal State Unitary Enterprise S.V. Lebedev Institute of Synthetic Rubber in Russia.

Preferred curatives and co-curatives for use in the fluoroelastomeric or perfluoroelastomeric compositions of the present invention are those which include functionalized diphenyl compounds which include branched or straight chain alkyl, halogenated alkyl, perhalogenated alkyl, and preferably perfluoroalkyl type compounds that may or may not have one or more oxygen atoms and which may or may not be substituted, and which have at least two aminophenyl groups, preferably two aminophenol groups, but which have a sufficiently high molecular weight (extended chains) so that the melting point is preferably no greater than about 240° C., more preferably no greater than about 230° C., and most preferably to about 225° C. to thereby enhance compatibility and provide fast curing reactions of perfluoroelastomeric compositions, particularly the preferred perfluoroelastomers having cyano-type curesite monomers.

Such curing agents are preferably diphenyl-based curatives of formula (III):

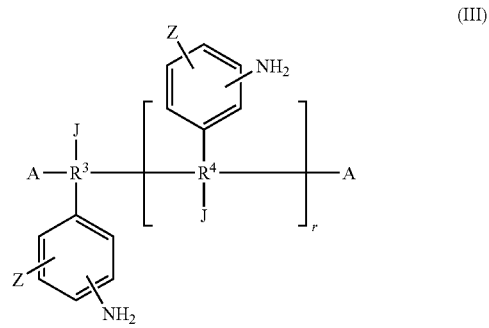

(III)

In formula (III), r may be 0 or 1. In formula (III), further $R^3$ and $R^4$ are independently selected to be a carbon atom or branched or straight chain carbon-based groups (which may be further substituted or unsubstituted) of from about 2 to about 22 carbon atoms in any of such chains (whether straight or branched), more preferably such chains are from 10 to 22 carbon atoms, and which groups are selected from the following exemplary groups: alkyl groups, fully or partially halogenated alkyl groups, and preferably perfluorinated alkyl groups, each of which groups may be interrupted by at least one oxygen atom, and in which branching chains may include such groups as, for example, haloalkyl, fluoroalkyl and trifluoroalkyl. Substitutions acceptable for use in formula (III) and other formulae described herein as containing substitutable groups, including the preferred formulations in accordance with formula (III) described below, may be the same as noted herein for formulas (I) and (II) to the extent such substitutions may be desired for a given curing reaction. Z is preferably an amino, mercapto, thiphenol, sulfhydryl or hydroxyl group, with the hydroxyl group being most preferred.

Each J is independently selected to be formula (IV):

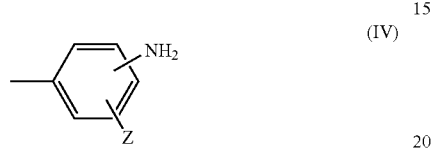

(IV)

or the same as A, and A may be independently selected on either side of $R^3$ in formula (III) to be formula (IV), a hydrogen atom, a fluorine atom, or a branched or straight chain (substituted or unsubstituted) carbon-based group which is selected from the following groups: an alkyl, a partially or fully halogenated alkyl, or perfluoroalkyl groups, more preferably a perfluoroalkyl group, of from one to about 22 carbon atoms; each of which groups may be interrupted by at least one oxygen atom, and in which branching chains may include such groups as, for example, haloalkyl, fluoroalkyl and trifluoroalkyl. When r is 0 and $R^3$ is a carbon atom, at least one of J and each A is not formula (IV). While it is within the scope of the invention for an A group to be formula (IV), it is preferred that only two such groups appear in curatives of formula (III), such that if r is 0 and J is formula (IV) above, it is preferred that neither A group is formula (IV).

Preferred structures when r=0 in formula (III) and J meets formula IV above, include structures where $R^3$ is a carbon atom and those in which $R^3$ is a straight or branched alkyl or perfluorinated alkyl group which may or may not contain oxygen. Further preferred are structures in which when r is 0, $R^3$ is a carbon atom, J is formula (IV), one A is trifluoromethyl and the other A is selected from the group consisting of linear and branched chain perfluoroalkyl and perfluoroalkylether groups of from 2 to 22 carbon atoms.

Preferred structures where r is 0, J meets formula IV and $R^3$ is a carbon atom include the following structures (V) through (VII) in which q preferably ranges from 0 to 6, however q being greater than 6 is also within the scope of the invention.

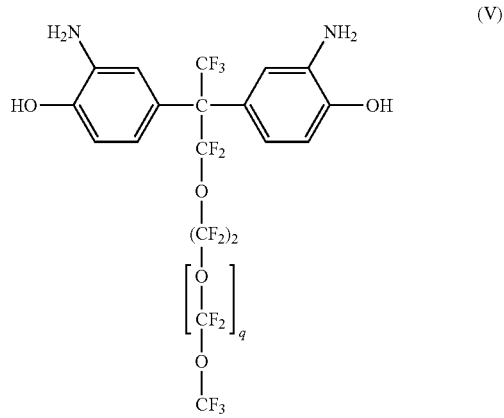

(V)

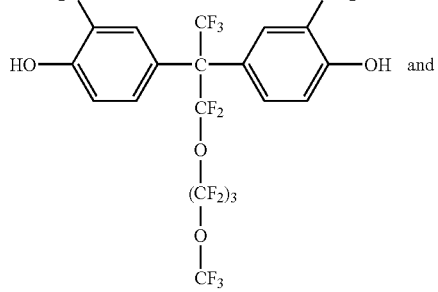

(VI)

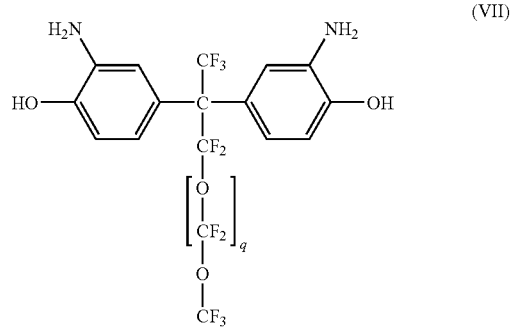

(VII)

Further preferred examples of formula III when r is 0, $R^3$ is a carbon atom, A is $CF_3$ on one side of $R^3$ and A is a chain of varied length on the other side of $R^3$ include the following materials as set forth in Table 1 below in accordance with the structure of the chain represented by the A group opposite the A which is $CF_3$. As can be seen from Table 1, the preferred compounds are similar in color and appearance but differ in melting point, providing a wider range of options for curatives in terms of compatibility and curing speed in fluoroelastomeric and perfluoroelastomeric compositions.

TABLE 1

| A | Color | Appearance | Melting Point (° C.) |
|---|---|---|---|
| $CF_3OCF_2CF_2OCF_2$ | White to creamy | powder | 210 |
| $CF_3OCF_2CF_2CF_2OCF_2$ | White to creamy | powder | 175 |
| $CF_3O(CF_2O)_2CF_2CF_2OCF_2$ | White to creamy | powder | 142 |
| $CF_3O(CF_2O)_3CF_2CF_2OCF_2$ | White to creamy | powder | 100 |
| $CF_3O(CF_2O)_4CF_2CF_2OCF_2$ | White to creamy | powder | 75 |
| $CF_3OCF_2$ | White to creamy | powder | 235 |
| $CF_3OCF_2OCF_2$ | White to Creamy | powder | 190 |
| $CF_3O(CF_2O)_2CF_2$ | White to Creamy | powder | 155 |
| $CF_3O(CF_2O)_3CF_2$ | White to Creamy | powder | 120 |
| $CF_3OCF_2CF_2CF_2OCF_2$ | White to Creamy | powder | 220 |

Preferred exemplary structures when r is 0 in formula (III), J is as in formula IV above and $R^3$ is a straight or branched chain group such as alkyl, halogenated alkyl, and preferably a perfluorinated alkyl group, which may or may not contain oxygen, include structures such as (VIII) and (IX) below in which the biaminophenyl groups are not in the bis position as are the structures shown above, but are in terminal positions separated by a chain providing a molecular weight which is sufficient to provide a melting point of no greater than about 240° C., more preferably no greater than about 230° C., and most preferably no greater than about 225° C. In such structures, A may be as described above. While it is within the scope of the invention for an A group to be formula (IV), it is preferred that when J is formula (IV), only two such groups appear in curatives of formula (III) and that it is preferred in such structures that neither A is formula (IV):

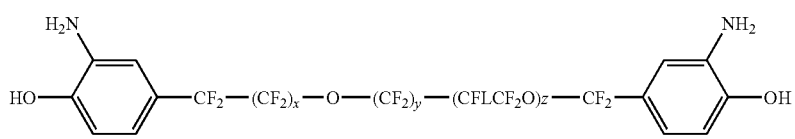

(VIII)

wherein x, y and z are each independently selected to be from 0 to about 20, preferably from 0 to 10, wherein preferably x+y+z total no more than about 20, and preferably from about 9 to about 20 and L is hydrogen, halogen such as fluorine, chlorine, bromine and iodine, alkyl, halogenated alkyl and preferably perfluorinated alkyls such as trifluoromethyl, most preferably L is fluorine or trifluoromethyl. A further example includes:

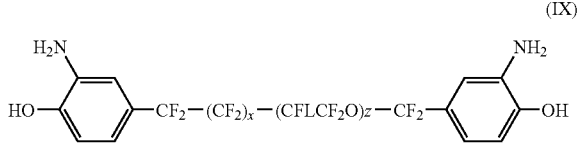

(IX)

wherein L, x, z are as defined above, but x and z are each independently preferably from 0 to about 10, and wherein x+y totals preferably no more than about 20, preferably from about 9 to about 20. It should be understood that structures in accordance with Formula (III) where r is 0 and $R^3$ is straight or branched alkyl or perfluorinated alkyl group which may or may not contain oxygen, include variations of formulae VIII and IX wherein fluorine atoms may be substituted and/or L may be branched into longer structures as shown below, for example in formulae X-XII:

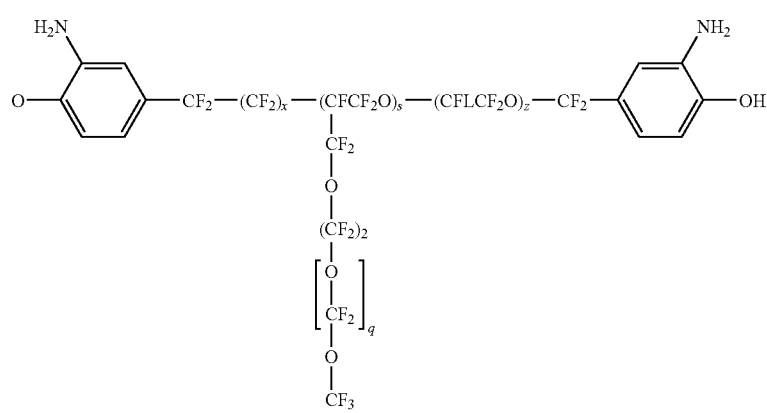

(X)

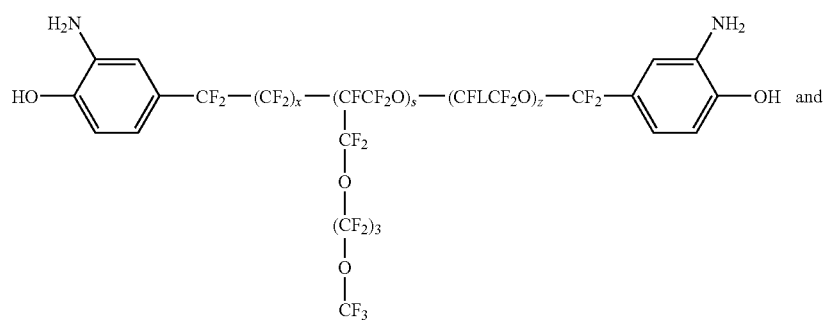

(XI)

and

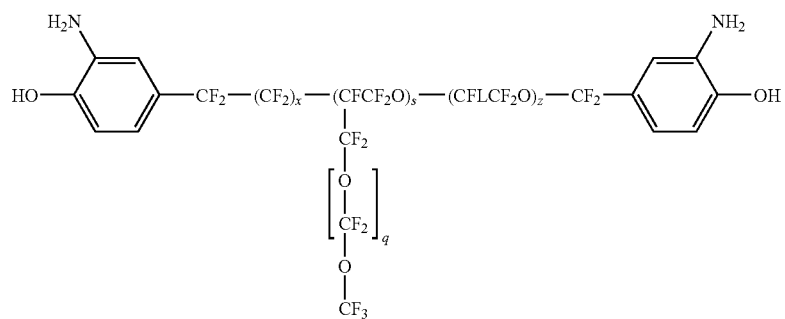

(XII)

wherein s is preferably 1 to about 6, and x, s and z are as previously defined, with x+s+z preferably totaling no more than about 20, and more preferably at a minimum, s is 1 and x and z are 0.

When r is not 0 in formula (III), structures are included within the scope of the invention which have at least two aminophenyl groups, but wherein the aminophenyl groups are not in the bis position and/or necessarily in a terminal position. In such structures, at least one aminophenyl group is located on $R^3$ and $R^4$ at any location along each of their chains, with J and A being as defined above, but in preferred embodiments, only two such aminophenyl groups are present in the compound as a whole such that when two such groups are already are present it is preferred that J and A are not formula (IV), even though such compounds are clearly contemplated as being within the scope of the invention. Exemplary such bisaminophenol structures are as follows, however it should be understand that variations of such structures are also included within the invention in accordance with formula (III):

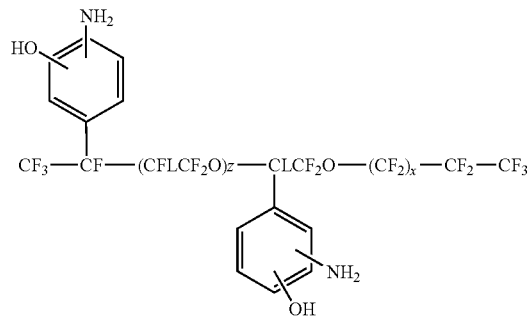
(XIII)

For example, in formula XIII above, both A groups are

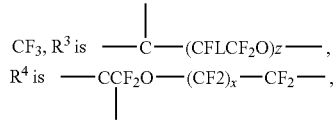

the J group on $R^3$ is F and the J group on $R^4$ is L, and x and z are as described below. Further examples include:

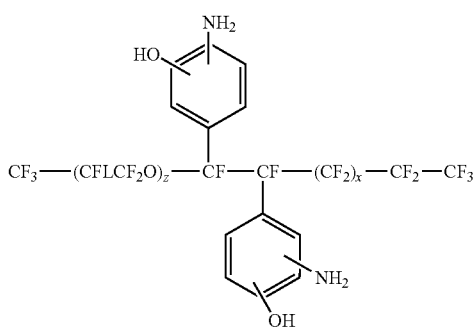
(XIV)

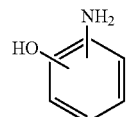
(XV)

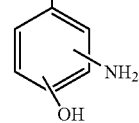

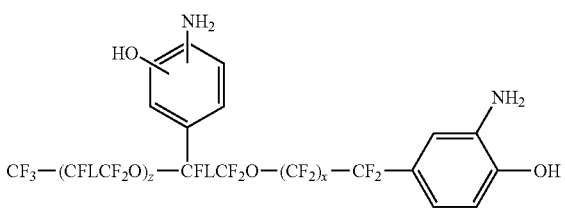
(XVI)

wherein L, x and z are as described above, however, in formula XIII, XIV, XV and XVI, it is preferred that and that x and z total no more than 19. It is also preferred that in all of the formula noted above, L is fluoro, perfluoroalkyl or perfluoroalkoxy.

Other preferred formula include formula (III), wherein when r is 1, each A and each J are fluorine, $R^3$ is a carbon atom and $R^4$ is selected from the group consisting of linear and branched chain perfluoroalkylene and perfluoroalkylether groups of from 2 to 22 carbon atoms, wherein one A and one J are both bonded to the terminal carbon atom of $R^4$.

Various synthetic routes exist and/or may be developed for making the various preferred curing agents according to formula (III). The curing agents are within the scope of the invention regardless of which chemical route is used to obtain them. Existing routes are described for making some of the compounds according to formula III as described in R. C. Evers, J. Polym. Sci. 16, 2833-2848 (1978), incorporated herein by reference. Further, the present invention includes several novel routes for preparing preferred compounds in accordance with formula (III). One route involves using epoxide-ketone reactions as described further below and another involves an organomagnesium route also described further herein. However, while novel methods are presented herein, it should be understood that any synthesis method may be used to make the novel curatives and co-curatives of the invention and that the invention of providing functionalized diphenyl-based curatives and co-curatives which have molecular weights sufficiently high to provide a melting point of no greater than about 240° C., more preferably no greater than about 230° C., or most preferably no greater than about 225° C. are encompassed within the invention including those having formula (III) regardless of their methods of synthesis.

Preferred reactions include reacting a perfluoroalkylacid halide, preferably a perfluoroalkyl acid fluoride, i.e., an acyl-group compound, preferably a perfluoroacyl fluoride with potassium fluoride to form an alcoholate of the initial compound. The potassium alcoholate reaction product, is then reacted with perfluoroallyl fluorosulfate to form the perfluoroallylether of that material.

This perfluoroallyl ether reactant product is then further reacted with an oxidizing agent, i.e., oxidized, wherein the oxidizing agent is preferably oxygen but is not limited thereto, to form a perfluoroglycidyl ether. The perfluoroglycidyl ether, which is then reacted with aluminum chloride in a fluorinated solvent, isomerizes the epoxide group on the perfluoroglycidyl ether to a ketone. The ketone compound is then reacted with a phenyl having functional group Z (preferably where Z is OH and the phenyl is phenol) in the presence of hydrogen fluoride to form a bisphenyl-based compound, preferably a bisphenol compound.

Such a bisphenyl- or bisphenol-based compound is then nitrated with nitric acid (or a similar useful nitrating compound) to provide an $NO_2$ group on each phenyl group and form a bisnitrophenyl-based or bisnitrophenol-based compound. This compound is then reduced using a suitable reducing agent to form the desired compound having bisaminophenyl, preferably bisaminophenol groups each having the Z radical (preferably bisaminophenol groups) of Formula IV which is capable of curing a perfluoroelastomeric composition.

Such an exemplary synthesis route for forming novel curatives and co-curatives according the invention may be illustrated with reference to structures such formulae V and VI and similar compounds where one A in formula III is $CF_3$, $R^3$ is a carbon atom, J is formula IV and r is 0, includes the following basic reaction scheme wherein R' refers to a portion of the chain that is part of the A group ($CF_2$—O—$CF_2$—R') extending opposite the A which is $CF_3$:

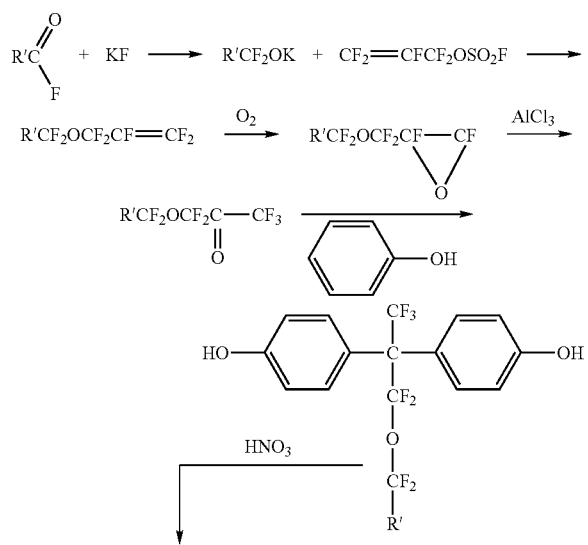

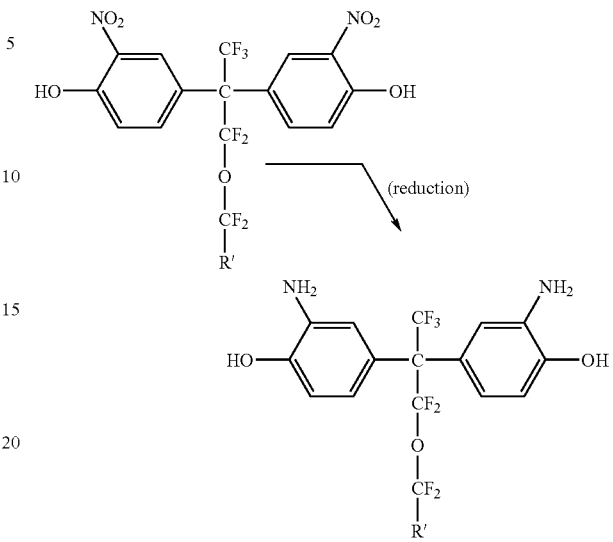

A further exemplary reaction scheme for forming compounds according to formula 3 (III) when $R^3$ is a carbon atom, r is 0, J is formula (IV), one A group is $CF_3$ and the other A group (referred to in the mechanism below as A') is $CF_3O(CF_2O)_qCF_2$— such as compounds in formula (VII) and similar compounds includes a method using organomagnesium compounds. In this synthesis route, an alkylmagnesium halide, halogenated alkyl magnesium halide or a perfluoroalkyl magnesium halide, and preferably a perfluoromagnesium iodide such as trifluoromethylmagnesium iodide is reacted with an alkyl, halogenated alkyl or perfluorinated acyl halide (such as an A chain in formula (III)) wherein the acyl halide includes a halogenated ketone group. The resulting compound releases magnesium halide to leave a ketone group on the acyl halide. This ketone is then further reacted with a substituted phenyl compound having a Z functional group (preferably hydroxyl) to form a bisphenyl functional group (preferably bisphenol) at the ketone site, which is then nitrated and subsequently reduced in the manner noted above. A sample of such mechanism is as shown below:

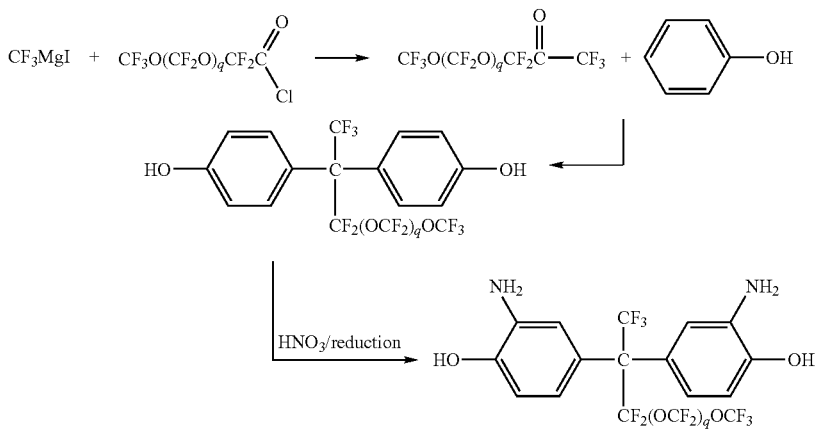

Alternatively, each of the two phenyl groups may be provided to R³ or R⁴ at different locations and/or terminal locations by using known chemical substitution techniques and routes to achieve various other formulae in accordance with formula (III). One such substitution route is shown in Evers, noted above herein, which obtains fluorocarbon bisaminophenols (some of which are represented by formula (III)) by reacting diiodoperfluoroalkane intermediates with iodophenyl acetate, hydrolyzing the product to obtain a bisphenol, nitrating and then reducing the dinitrobisphenol to obtain a bisaminophenol.

It also possible to employ other curing agents or more than one curing agent depending on the cure site monomers present, such as an organic peroxide, an organometallic compound such as an organotin, diamines, amidines, conventional bisaminophenols and/or bisaminothiophenols, etc. or mixtures thereof. In addition, perfluoropolymers may be cured using radiation curing technology as an assist or to cure other curesites not cured by the curatives and co-curatives of the invention.

The amount and type of curative or co-curing agent according to the invention which should be used should be chosen to optimize the desired properties of the cured fluoroelastomer or perfluoroelastomer (including its resistance to chemical attack, specific elongation-at-break, resistance to compression set, flexural modulus, tear strength, hardness and the like). The amount used will depend on the degree of crosslinking desired, the type and number of cure sites to be cured by the inventive curatives, the number of other cure sites to be cured by other curatives not within the scope of the invention, and the cure rate desired. A preferred amount of curative is an amount as much as equivalent to an amount in slight excess of the amount required to react with those curesites present in the fluoroelastomeric or perfluoroelastomeric composition which are capable of reacting with the curatives and co-curatives of the invention. Preferably, about 0.1 to about 10 parts by weight of the curing agent per about 100 parts of fluoropolymer or perfluoropolymer is used, more preferably about 1 to about 4 parts by weight. When used as a co-curative, the amount is preferably less, since other cure reactions are occurring, however, that too depends on the number of sites and other parameters noted above.

The invention includes amidine-based or amidoxime-based curatives which may function as curatives or co-curatives, and also as cure accelerators, and may be employed either alone or with the biphenyl-based curatives and co-curatives of the invention as described herein or with other curatives not within the invention, or used to further accelerate the rate of cure of the biphenyl-based curatives and co-curatives of the invention nor other curatives outside of the invention within perfluoroelastomeric compositions.

Suitable amidine and amidoxime curatives and accelerators include monoamidines, monoamidoximes and bisamidines as described herein. Other cure accelerators known in the art such as organic or inorganic ammoniums salts, e.g. perfluoroctonaoate, ammonium perfluoroacetate, ammonium thiocyanate, and ammonium sulfamate; urea; t-butyl carbamate; acetaldehyde ammonia; tetraalkylphosphonium salts, tetraalkylammonium salts, and trialkylsulfonium salts, such as benzyltriphenylphosphonium chloride, benzyltriphenylphosphonium bromide, benzyltriphenyl-phosphonium phenolate of bisphenol AF, tetrabutylammonium hydrogen sulfate, and tetrabutylammonium bromide may also be used in conjunction with the novel biphenyl-based curatives and co-curatives of the invention if desired. However, of accelerators are desired for the novel biphenyl-based curatives and co-curatives of the invention, it is preferred that the amidine- and amidoxime-based cure accelerators described herein be used to accelerate the cure of the biphenyl-based curatives and co-curatives of the invention.

The preferred accelerators for the biphenyl-based curatives and co-curatives of the present invention are amidine-based and amidoxime-based cure accelerators, which also may themselves function as independent curatives or co-curatives in perfluoroelastomeric compositions. These amidine-based and amidoxime-based materials include monoamidines and monoamidoximes of the following formula (I) and bisamidines of formula (II) described further below. The monoamidines and monoamidoximes may be represented by formula (I)

wherein Y may be a substituted alkyl, alkoxy, aryl, aralkyl or aralkoxy group or an unsubstituted or substituted fully or partially halogenated alkyl, alkoxy, aryl, aralkyl or aralkoxy group having from about 1 to about 22 carbon atoms. Y may also be, and preferably is, a perfluoroalkyl, perfluoroalkoxy, perfluoroaryl, perfluoroaralkyl or perfluoroaralkoxy group of from 1 to about 22 carbon atoms and more preferably a perfluoroalkyl or perfluoroalkoxy group of from about 1 to about 12 carbon atoms, and more preferably from 1 to 9 carbon atoms; and $R^1$ may be hydrogen or substituted or unsubstituted lower alkyl or alkoxy groups of from one to about 6 carbon atoms, or an amino group. $R^2$ may be independently any of the groups listed above for $R^1$ or hydroxyl. Substituted groups for Y. $R^1$ or $R^2$ include, without limitation, halogenated alkyl, perhalogenated alkyl, halogenated alkoxy, perhalogenated alkoxy, thio, amine, imine, amide, imide, halogen, carboxyl, sulfonyl, hydroxyl, and the like. Preferred embodiments include those in which $R^2$ is hydroxyl, hydrogen or substituted or unsubstituted alkyl or alkoxy groups of from 1 to 6 carbon atoms, more preferably hydroxyl or hydrogen. Also preferred are embodiments in which $R^1$ is hydrogen, amino or a substituted or unsubstituted lower alkyl of from 1 to 6 carbon atoms while $R^2$ is hydrogen or hydroxyl. Most preferred are embodiments where $R^1$ is hydrogen. Further preferred embodiments include those in which Y is perfluoroalkyl, perfluoroalkoxy, substituted or unsubstituted aryl groups and substituted or unsubstituted halogenated aryl groups having the chain lengths as noted above.

Exemplary monoamidine-based and monoamidoxime-based curatives according to formula (I) include perfluoroalkylamidines, arylamidines, perfluoroalkylamidoximes, arylamidoximes and perfluoroalkylamidrazones. Specific examples include perfluorooctanamidine, heptafluorobutyrylamidine, benzamidine, trifluoromethylbenzamidoxime, and trifluoromethoxylbenzamidoxime. Curatives as noted according to formula (I) may be used alone or in combinations, such as combinations of the foregoing exemplary compounds.

The curatives according to formula (I) are preferably capable of curing perfluoroelastomeric compositions, particularly those with at least one cyano curesite monomer. The curatives according to formula (I) of the present invention are also monoamidine-based and monoamidoxime-based cure accelerators which are capable of accelerating the cure of perfluoroelastomeric compositions comprising at least one cyano curesite monomer, and more preferably compositions which also include diphenyl-based curatives (including the novel diphenyl-based curatives of the invention), such as bisaminophenol and its derivatives. Suitable examples of monoamidines include benzamidines and perfluoroalkyl amidines. Particularly suitable examples are perfluorooctanamidine and perfluoroheptanamidine.

The invention also includes bisamidine-based curative and cure accelerators for fluoroelastomeric and perfluoroelastomeric compositions represented by formula (II):

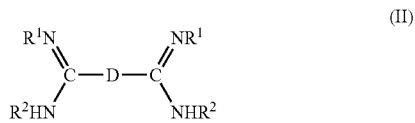

wherein D may be unsubstituted or substituted fully or partially halogenated alkyl, alkoxy, aryl, aralkyl or aralkoxy groups having from about 1 to about 22 carbon atoms, or more preferably perfluoroalkyl, perfluoroalkoxy, perfluoroaryl, perfluoroaralkyl, or perfluoroaralkoxy groups of from 1 to about 22 carbon atoms and more preferably a perfluoroalkyl or perfluoroalkoxy group of from about 1 to about 12 carbon atoms. $R^1$ and $R^2$ are as defined above with respect to formula (I), however, in formula (II), $R^2$ is not hydroxyl, it is independently selected to be the same as $R^1$ noted above. Further, D, $R^1$ and $R^2$ may each be substituted by one of more of the groups noted above with respect to formula (I). Most preferably herein in formula (II), both $R^1$ and $R^2$ are hydrogen.

Oxygen atoms are preferably included in the form of ether linkages in Y, $R^1$ and $R^2$ While it is preferred that Y is straight or branched, it is also within the scope of the invention that Y could be a cyclic or aromatic structure, which is capable of being substituted as noted above.

With respect to the bisamidines of formula (II), it is preferable that D is a fluorinated, more preferably perfluorinated. If D is only partially halogenated, however, it is preferred that the carbon atoms adjacent the amidine groups each have two hydrogen substituents to stabilize the compound. Oxygen atoms in D are preferably also in the form of ether linkages. While it is preferred that D is straight or branched chain, it is also within the scope of the invention that D is a cyclic or aromatic structure, which may be further substituted. Particularly suitable examples of such bisamidines include perfluorosuberamidine and perfluorosebacamidine. Suitable perfluoroalkyl monoamidines and bisamidines can be purchased from SynQuest Laboratories, Inc. of Alachua, Fla. Such materials are commercially available from Federal State Unitary Enterprise S.V. Lebedev Institute of Synthetic Rubber in Russia.

The bisamidines of the invention can be used as cure accelerators capable of accelerating the cure of perfluoroelastomers, particularly when the perfluoroelastomeric composition includes at least one cyano curesite monomer. Preferred exemplary bisamidines according to the invention include perfluorosuberamidine and perfluorosebacamidine.

It is understood that when the above amidine, amidoxime materials are used as accelerators, the amount is chosen may be based upon the particular perfluoroelastomer chosen, the curatives and/or co-curatives chosen and the desired cure properties, such as the time necessary to develop a minimum specified Mooney viscosity, the ability of the composition to resist deformation, and a maximum specified torque measured by a moving die rheometer. Suitable amounts include about 0.1 to about 5 parts of accelerator per about 100 parts of perfluoropolymer.

In preparing monoamidines, monoamidoximes and bisamidines, the invention is not restricted with respect to any particular synthesis method for making these compounds. Any chemical synthesis and/or use of commercially available monoamidines, monoamidoximes and bisamidines are acceptable. However, the present invention does include a novel synthesis method as described herein. With respect to preparing monoamidines useful within the invention, an alkyl acid (i.e., an organic acid such as a carboxylic acid containing compound), halogenated alkyl acid and preferably a perfluorinated alkyl acid is first converted to a nitrile form by combining the alkyl acid (or similar compound as noted) with an alcohol, such as an alkanol, e.g. methanol or ethanol in the presence of an inorganic acid such as sulfuric acid. The mixture is boiled, washed with water and dried, preferably using an suitable material such as $MgSO_4$. The resulting product is an alkylester, halogenated alkyl ester or perfluoroalkyl ester which is then reacted with a nitrogen containing reactant such as ammonia, preferably ammonia gas. A reaction is allowed to proceed with control of the reaction temperature to produce a carboxyamide structure, such as an alkylcarboxyamide. This reaction product is then combined with a dehydrating agent, such as, for example, phosphorus pentaoxide, mixed and refluxed under heat and the product is converted to an alkyl nitrile, such as cyano-functional alkyls including an alkylcyano, halogenated cyano or perfluoroalkyl cyano compounds. The alkyl nitrile compound is then added to a reaction chamber filled with at least one nitrogen containing compound, such as preferably an amine compound or ammonia in liquid or gas form, preferably in liquid form. It is preferred that the nitrogen-containing compound such as ammonia is present in excess, preferably about 10 fold excess, with respect to the added alkyl nitrile (preferably cyano-functional) compound. After addition of the alkyl nitrile compound to the chamber including the nitrogen containing compound, the temperature is raised, preferably slowly, to about ambient temperature and excess nitrogen containing compound (such as ammonia) is removed. Solid white product is typically the resulting compound which is an alkyl, halogenated alkyl or perfluorinated alkyl group having a monoamidine structure. While the foregoing represents a preferred synthesis route for making monoamidines according to the invention, any method known or to be developed may be employed in making the bisamidines, monoamidines or monoamidoximes of the invention without departing from the scope of the invention. The resulting monoamidines and monoamidoximes of the invention are useful as curatives and are capable of curing or accelerating the cure of perfluoroelastomeric compositions as noted above. Preferred compounds made according to the above method include perfluoroheptanamidine.

The perfluoroelastomeric composition is mixed or blended with any of the above additives by any conventional means or apparatus, including with two-roll mills and internal mixers. For example, the composition may be blended using an internal mixer such as those commercially available from Banbury, C.W. Bradender Instruments, Inc. of Hackensack, N.J. and from Morijama of Farmingdale, N.Y. Preferably, the curative(s) and co-curative(s) of the invention and/or the cure accelerators of the invention are added once all of the other ingredients desired are blended, however, it should be understood that the order in which such materials are provided is not limiting the scope of the invention. The curable compositions may then be processed and cured/crosslinked by application of heat and/or pressure to form an elastomeric part, such as a seal. After curing, postcuring may be desirable to enhance physical properties and is also within the scope of the invention.

Additional specific examples of preferred monoamidine cure accelerators, which may also be used as direct curative(s) or co-curative(s) are as found in Table 2, wherein $R^1$ and $R^2$ are both hydrogen and the compounds are categorized by the composition of Y in formula (I) above.

TABLE 2

| Y | Color | Appearance | Melting Point ° C. | UV Spectrum (nm) |
|---|---|---|---|---|
| —$CF_3$ | White to creamy | liquid | Tboiling = 40-44 (14 mm Hg) | 212 |
| —$C_2F_5$ | White to creamy | powder | 50 | 212 |
| —$C_3F_7$ | White to creamy | powder | 52 | 212 |
| —$C_4F_9$ | White to creamy | powder | 58 | 212 |
| —$C_5F_{11}$ | White to creamy | powder | 66 | 212 |
| —$C_6F_{13}$ | White to creamy | powder | 75 | 212 |
| —$C_7F_{15}$ | White to creamy | powder | 87 | 212 |
| —$C_8F_{17}$ | White to creamy | powder | 98 | 212 |
| —$C_9F_{19}$ | White to creamy | powder | 116 | 212 |

The invention will now be described by reference to the following non-limiting examples:

EXAMPLE 1

A bisaminophenol derivative according to formula (III) (2,2-bis[3-amino-4-hydroxyphenyl]4,7,9,11 tetraoxa-1,1,1,3,3,5,5,6,6,8,8,10,10,12,12,12-hexadecafluorododecane) was prepared in which $R^3$ is a carbon atom, r is 0, J is a structure as in formula (IV), one A is —$CF_3$ and the other A is —$CF_2OCF_2CF(OCF_2)_2OCF_3$. Such structure is shown above in representative form in formula (V). In preparing such compound, a perfluorinated polyether ketone was first formed in accordance with an epoxide-ketone route as described herein. A flask protected by a continuous flow of dry nitrogen gas was charged with potassium fluoride in an amount of 11.6 g (0.2 mole) and 100 ml Diglyme that had already been dried by distillation from $CaH_2$. The mixture was stirred for 15 minutes. To this mixture was added at room temperature with good stirring 60 g (0.19 mole) of 3,5,7-trioxa-2,2,4,4,6,6,8,8,8-nonafluorooctanoyl fluoride were added for 1 to 1.5 hours, at room temperature and with adequate stirring. After addition was completed, the mixture was stirred an additional 2 hours until all the potassium fluoride was dissolved forming the potassium alcoholate salt, $CF_3O(CF_2O)_2CF_2CF_2OK$. The presence of the alcoholate and completion of the reaction was confirmed by the disappearance of the acid fluoride band at 1890 cm$^{-1}$ in the infrared spectrum. The line 1890 cm$^{-1}$ corresponds to:

The reaction described above is characterized by the following:

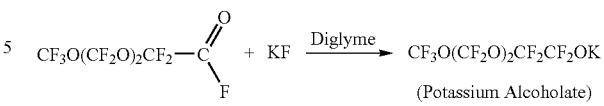

Following formation of the alcoholate above, the flask containing the above potassium alcoholate solution was cooled to 10° C. and a dropping funnel was attached. Perfluoroallylfluorosulfate in an amount of 48 g (0.21 mol) was then added slowly (dropwise) through a dropping funnel with a temperature of 10 to 15° C. being maintained. After an additional two hours stirring, two liquid layers formed. the layers were separated and the upper layer was distilled at a temperature of 60° C. under a vacuum of 0.5 mm Hg. The distillate was combined with the bottom layer. The crude product was washed with water to remove the $KOSO_2F$ salt, separated and the upper aqueous layer discarded. The lower layer was dried by distillation from $P_2O_5$ to obtain crude perfluoroallyl ether (4,7,9,11-tetraoxa-1,1,2,3,3,5,5,8,8,10,10,12,12,12-hexadecafluorododecene) in 95% yield. The crude perfluoroallyl ether was fractionally distilled and a fraction boiling at 88° C. was collected and identified by $F^{19}$ NMR, IR spectroscopy (absorption band at 1795 cm$^{-1}$ corresponding to —CF=$CF_2$) and elemental analysis. The elemental analysis is as follows:

calculated for $C_8F_{16}O_4$: C, 20.68%; F, 65.51%
experimentally found: C, 20.24%; F, 65.63%.

The reaction described above is shown representatively below:

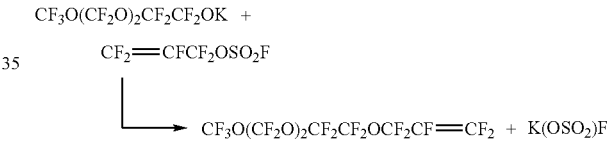

The above perfluoroallyl ether was oxidized in a well-agitated 1-liter stainless steel reactor. The reaction was carried out for 12 hours at a temperature of 80 to 120° C. and an oxygen pressure of 12 to 20 atm gauge (150 to 300 psig). The reaction mixture was distilled at 90° C. and a pressure of 100 mm Hg to yield the perfluoroglycidylether (4,7,9,11-tetraoxa-1,1,2,3,3,5,5,6,6,8,8,10,10,12,12,12-hexadecafluorododecane-1,2-oxirane) in 85% yield. The structure was confirmed by $F^{19}$ NMR, the presence of an IR band at 1530 cm$^{-1}$ (epoxide) corresponding to epoxide

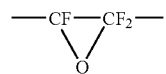

and the absence of an IR band at 1795 cm$^{-1}$ (absence of —CF=$CF_2$—). The reaction noted above is shown representatively below:

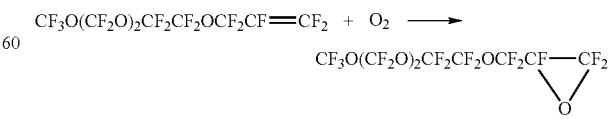

A flask was charged with three (3) g of $AlCl_3$ and 10 ml Freon 113 and the mixture was stirred at room temperature for 40 minutes. Most of the Freon 113 was removed at reduced pressure leaving a pasty residual. To this was added dropwise with stirring 30 g of the above perfluoroglycidyl ether over a period of 10 to 15 minutes. The mixture was then stirred at 50° C. for 2 hours. The course of the isomerization was monitored by infrared spectroscopy. The epoxide band at 1530 cm⁻ was replaced by the ketone band at 1796 cm$^{-1}$. Crude perfluoroketone was isolated in 90% yield by distillation at 60° C. and 100 mm Hg. The pure perfluoroketone (4,7,9,11-tetraoxa-1,1,1,3,3,5,5,6,6,8,8,10,10,12,12,12-hexadecafluorododecan-2-one) was obtained by fractional distillation at b.p. of 114° C. Its identity was confirmed by F$^{19}$ NMR and its purity by gas-liquid chromatography. The final reaction to form the perfluoroketone is shown representatively below:

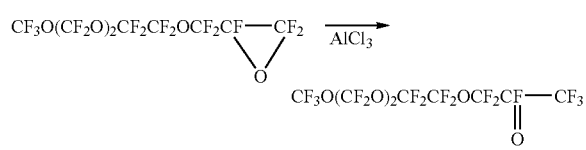

A metal ampoule was charged with 94 g of phenol, 240 g of perfluoroketone and 100 g of hydrogen fluoride, sealed and heated for 10 hours at a temperature of 95° C. The hydrogen fluoride was removed by distillation and the solid bis-phenol was purified by recrystallization from toluene and chloroform. The yield was pure bisphenol (2,2-bis[4-hydoxyphenyl]4,7,9,11-tetraoxa-1,1,1,3,3,5,5,6,6,8,8,10,10,12,12,12-hexadecafluorododecane) at 89%. The structure was confirmed by F$^{19}$ NMR.

A four-neck flask was fitted with an agitator, reflux condenser, dropping funnel and thermometer. A solution of 39.2 g of the above bisphenol product and 0.1 g NaNO$_2$ in 130 ml glacial acetic acid was prepared in the flask. With the solution maintained at 40-45° C., a solution of nitric acid and 20 ml glacial acetic acid was added. When the addition was completed the reaction mixture was heated for 2 hours at a temperature of 60° C., then for 3 hours at a temperature of 80° C. Water was added and the yellow-red oil that resulted was separated, dissolved in toluene and dried over MgSO$_4$. Toluene solvent was distilled off at 200-300 mm Hg pressure using a water-jet pump. The residual bisaminophenol product (2,2-bis[3-nitro-4-hydroxyphenyl]4,7,9,11-tetraoxa-1,1,1,3,3,5,5,6,6,8,8,10,10,12,12,12-hexadecafluorododecane) was obtained in an amount of 54.7 g for a 81.1% yield.

A four-neck flask was fitted with an agitator, reflux condenser, dropping funnel and thermometer. A solution of the bisaminophenol above in 100 ml ethanol was prepared in the flask and 1.5 g catalyst was added (5% Pt on carbon). With agitation, 12 g of 100% hydrogen peroxide was added and the mixture was refluxed for 4 hours. The mixture was cooled filtered to remove the catalyst and diluted with three volumes of water. The aqueous mixture was acidified with acetic acid to a pH below 6. The precipitated product was collected by filtration, air-dried and recrystallized from ethyl acetate. Pure bisaminophenol (2,2-bis[3-amino-4-hydroxyphenyl]4,7,9,11-tetraoxa-1,1,1,3,3,5,5,6,6,8,8,10,10,12,12,12-hexadecafluorododecane) product melting at 142° C. was obtained in 91.0% yield (45.7 g). The structure was confirmed by F$^{19}$ NMR.

EXAMPLE 2

In making the same bisaminophenol derivative product as in Example 1, an alternate route was taken to prepare the perfluoroketone using organomagnesium synthesis which involves condensation of trifluoromethyl magnesium iodide with a perfluoroalkanoyl halide. The synthesis is described in J.Am.Chem.Soc., pp. 1273-77 (1954):

A flask containing 28.8 g Mg and a few crystals of iodine was heated with stirring to 60° C. until the iodine color disappeared. The flask was cooled to room temperature and 300 ml of diethyl ether were added. The flask cooled to −40° C. and 19.0 g of CF$_3$I were slowly added dropwise over a period of 3 hours to produce a solution containing 8.8 g (40% yield) of CF$_3$MgI. The temperature was raised to 30° C., and 3,5,7-trioxa-2,2,4,4,6,6,8,8,8-nonafluorooctanoyl chloride) was added over a period of one hour while stirring. After an additional 7 hours stirring at room temperature the perfluoroketone product, 4,6,8-trioxa-1,1,1,3,3,5,5,7,7,9,9,9-dodecafluorononan-2one, was isolated by distillation at reduced pressure (b.p. of 1° C. at 15 mm Hg). The structure was confirmed using F NMR. This perfluoroketone can be converted via the procedures described in Example 1 to form a bisaminophenol (2,2-bis[3-amino-4-hydroxyphenyl]4,6,8-tetraoxa-1,1,1,3,3,5,5,7,7,9,9,9-dodecafluorononane) with melting point 115° C.

EXAMPLE 3

Monoamidines were synthesized in accordance with the method of the invention as follows. In a four-neck flask, provided with a mixer, thermometer, back-flow condenser and a dropping funnel, 41.1 g (0.01 mole) of dry C$_7$F$_{15}$COOH were added and blended with 32.0 g methanol and 19. ml of concentrated H$_2$SO$_4$. The mixture was boiled for 6 hours, then washed with water and dried with MgSO$_4$. The product, an ester, was distilled (T$_{boiling}$ of 158° C.). The yield was 90-95% (39.2 g) using the procedure as described in U.S. Pat. No. 2,570,116 (1951). In a four-neck flask, provided with mixer, thermometer, condenser and the tube for introduction of gas, 39.2 g of C$_7$F$_{15}$COOCH$_3$ and 100 ml diethyl ether were added. Additionally, ammonia gas was provided, and ice was used as necessary to cool the flask. The completion of the reaction was checked by gas-liquid chromatography by noting the absence of C$_7$F$_{15}$COOCH$_3$ in the ether solution. The ether was distilled off, and the solid product was dried in air. 37.0 g of C$_7$F$_{15}$CONH$_2$ were obtained (a yield of 97.9%) and the product had a T$_{boiling}$ of 90° C. In a round-bottom flask, 37.0 g of C$_7$F$_{15}$CONH$_2$ (0.0896 mol) that had been ground into a fine powder and 63.6 g of P$_2$O$_5$ were added. The materials were thoroughly mixed, and a reflux condenser was placed on the flask and heated at 100-200° C. The product C$_7$F$_{15}$—CN was obtained in an amount of 30.1 g (a yield of 85%), and had a T$_{boiling}$ of 90° C. The reaction scheme as noted above appears representatively below:

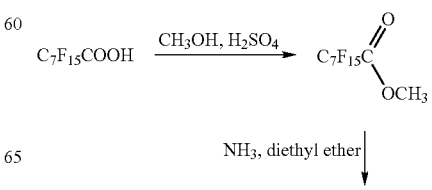

-continued

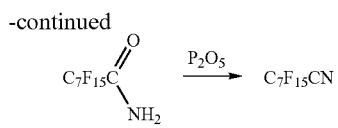

Such cyano terminal compound was then converted to monoamidine form having a formula $C_7F_{15}CN$ using a technique such as that used in Example 4 below.

EXAMPLE 4

A ten-fold excess, fifty (50) ml, of anhydrous ammonia gas were condensed into a four-neck flask fitted with an agitator, reflux condenser, dropping funnel, thermometer, and a drying tube (filled with solid KOH) which had been cooled in a dry ice/ethanol bath. The ammonia was condensed into the flask via the drying tube. With good agitation and cooling, 60 g of a reaction product (perfluoroheptanonitrile), made in accordance with the technique described in Example 4 for conversion of a perfluoroacid to a nitrile, having the structure $C_6F_{13}CN$ was added slowly. After addition was completed, the temperature was allowed to slowly rise to ambient allowing the excess ammonia to evaporate. The resulting white solid product was air dried to yield 62.0 g of perfluoroheptanamide having the following formula (a yield of 98.5% with a m.p. at 75-76° C.).

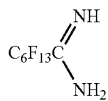

Ultraviolet spectroscopy showed a characteristic amidine absorption band at 212 nm, for the group

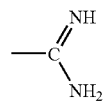

and an extinction coefficient, $\epsilon = 6098$.

EXAMPLE 5

In this example, various perfluoroelastomeric compositions were prepared using as a base perfluoroelastomer, tetrapolymers prepared by batchwise polymerization in aqueous emulsion as described in detail in WO 00/08076, incorporated herein by reference. The monomers in the terpolymer included tetrafluoroethylene, perfluoromethylvinyl ether and two curesite monomers, a secondary cyano curesite monomer, $CF_2=CFO(CF_2)_3OCF(CF_3)CN$ and a primary cyano curesite monomer, $CF_2=CFOCF_2CF(CF_3)O(CF_2)_2CN$. Polymerizations were conducted in an aqueous emulsion containing 1,1,2-trichloro-1,2,2-trifluoroethane using ammonium persulfate or ammonium persulfate/sodium sulfite redox intiation. The surfactant mixture included ammonium perfluoroheptanoate and ammonium perfluorononanoate. The buffer used was dipotassium phosphate. Tetrapolymers were isolated by coagulation with magnesium chloride, washed with hot water and alcohol and dried at 60° C. The composition was determined by $F^{19}NMR$ and elemental analysis for carbon and fluorine. Mooney viscosity was measured at 100° C. on a TechPro® viscTECH TPD-1585 viscometer. The following four tetrapolymers made in accordance with the foregoing method and having the foregoing composition were used in the formulations made in accordance with the invention:

Polymer A: redox type, 45 Mooney viscosity
Polymer B: non-redox, 65 Mooney viscosity
Polymer C: non-redox, 64 Mooney viscosity
Polymer D: non-redox, 93 Mooney viscosity To the polymers noted above, used in these compositions, were added various curatives and combinations of curatives, including: perfluorosebacamidine and perfluorooctanamidine both of which were from obtained from SynQuest Laboratories, Inc., Alachua, Florida, and perfluorosuberamidine and perfluoroheptanamidine which were obtained from Federal State Unitary Enterprise S.V. Lebedev Institute of Synthetic Rubber in Russia. Perfluorocarbon ether oil was also used in various compositions as an additive, and is available from DuPont Specialty Chemicals, Wilmington, Del. Standard BOAP (2,2-bis[3-amino-4-hydroxyphenol]hexafluoropropane) was purchased from TCI America, Portland, Oreg. Both of the diaminophenol curatives used in the compositions, Curatives A and B were obtained from Federal State Unitary Enterprise S.V. Lebedev Institute of Synthetic Rubber in Russia. Curatives A and B each had the structure: (2,2,-bis[3-amino-4-hydroxylphenol]R). In Curative A, R was $-CF_2(OCF_2)_3OCF_3$, Curative A had a melting point of 120° C. and a molecular weight of 630 daltons. In Curative B, R was $-CF_2OCF_2CF_2(OCF_2)_2OCF_3$ and Curative B had a melting point of about 142 to 145° C. and a molecular weight of 680 daltons. Also used in the exemplary compositions herein is carbon black, specifically Carbon Black N990.

Test specimens were made by mixing a tetrapolymer and the curatives to form a perfluoroelastomeric composition, and adding carbon black to that composition, using a Brabender 100 g or 600 g internal mixer. The compounds, upon mixing, were shaped into O-ring preforms, molded to cure the performs into seals and then postcured into Size 214 O-rings in accordance with the cure and postcure conditions noted in the Tables below. The rings were tested for tensile properties using ASTM-D-412, Method B, and the following parameters were recorded: TB (tensile at break in MPa); EB (elongation at break in %); and $M_{100}$ (modulus at 100% elongation in MPa). Compression set of O-ring samples was determined in accordance with ASTM-D-395, Method B. Cure characteristics were measured using a Monsanto MDR 2000 under the following conditions:

Moving die frequency: 1.6667 Hz
Oscillation amplitude: 0.5 deg arc
Temperature: as indicated in Tables herein
Sample size: disks of 1.6 inch diameter, thickness of 0.17 inch and 9.5 g weight
Duration of test: 60 minutes The following cure parameters were recorded: $M_H$ (maximum torque level in units of Nm); $M_L$ (minimum torque level in unites of Nm); $t_S2$ (minutes to 0.23 Nm rise above $M_L$); and $t_C90$ (minutes to 90% of $M_H$.

Tables 3 and 4 (Samples Nos. 1-12) are directed to use of novel curatives, Curatives A and B, and to use of novel amidines and bisamidines as cure accelerators for those novel curatives as well as for standard BOAP, and includes the use of BOAP alone as a comparative sample (Sample No. 11). The compositions include a tetrapolymer, one of Polymers A-D, Carbon Black N990 and Fluorogard PCA. In Table 4, the cure characteristics (except as noted) were MDR, 1 h@160° C. Table 3 includes the formulations and Table 4 includes the data related to those formulations.

Table 5 includes data showing the effects of use of bisamidines and monoamidines of the invention as curatives (Samples Nos. 13-19). Each of these compositions is based on Polymer A, and includes Fluorogard PCA and Carbon Black N990 as additives. In each of Samples 13-19, 100 phr of Polymer A were mixed with 25 phr carbon black and 1.5 phr Fluorogard PCA. The varying amounts of curatives are shown in Table 5 along with the resulting data for each perfluoroelastomeric composition. In Table 5, when the post cure sequence G is used, it represents increasing the temperature from 25° C. to 94° C. over 1.5 h and then to 149° C. over 1 h. The post cure is then held at 149° C. for 0.5 h and then further heated to 204° C. over 1 h and held at 204° C. for 18 h. The temperature is then increased to 260° C. over 1 h and held at that temperature for 18 h. The post cure is then cooled to 25° C. over 2 h.

Tables 6 and 7 include compositions and data, respectively, directed to the effect of bisamidines and monoamidines as cure accelerators for BOAP containing perfluoroelastomeric compositions. In Samples Nos. 20-30, Polymers A, B and D compositions each including 100 phr of the polymer, 25 phr Carbon Black N990, 1.5 phr Fluorogard PCA and varying amounts of BOAP are cured with the amidines as indicated. The data demonstrate the acceleration affect of the amidine cure accelerators of the invention.

TABLE 3

| | Sample | | | | | | | | | | | |
|---|---|---|---|---|---|---|---|---|---|---|---|---|
| | 1 | 2 | 3 | 4 | 5 | 6 | 7 | 8 | 9 | 10 | 11* | 12 |
| Polymer A | 100 | | | | | | | | | | | |
| Polymer B | | 100 | 100 | 100 | 100 | 100 | 100 | 100 | | | | |
| Polymer C | | | | | | | | | | | 100 | 100 |
| Polymer D | | | | | | | | | 100 | 100 | | |
| Carbon Black N990 | 25 | 25 | 25 | 25 | 25 | 25 | 25 | 25 | 25 | 25 | 25 | 25 |
| Fluorogard PCA | 1.5 | 1.5 | 1.5 | 1.5 | 1.5 | 1.5 | 1.5 | 1.5 | 1.5 | 1.5 | 1.5 | 1.5 |
| BOAP | | | | | | | | | 1¥ | | 1¥ | |
| Curative A | 1.8 | 1.8 | 1 | 1.5 | 2.5 | 3 | 3 | 4 | | 2£ | | |
| Curative B | | | | | | | | | | | | 1.9α |
| Perfluorooctanamidine | | | 1 | 1.5 | 1.5 | 1 | 1.5 | 2 | 1.25 | 1.25 | | |

*Comparative Sample
¥2.27 mmol
£3.2 mmol
α2.8 mmol

TABLE 4

| | Sample | | | | | | | | | | | |
|---|---|---|---|---|---|---|---|---|---|---|---|---|
| | 1β | 2β | 3 | 4 | 5 | 6 | 7 | 8 | 9β | 10 | 11*β | 12 |
| $M_L$ (lb-in) | 0.24 | 0.44 | 0.98 | 1.41 | 1.08 | 0.95 | 1.22 | 1.38 | 1.56 | 1.33 | | |
| $M_L$ (Nm) | 0.03 | 0.05 | 0.11 | 0.16 | 0.12 | 0.11 | 0.14 | 0.16 | 0.18 | 0.15 | 0.11 | 0.44 |
| $M_H$ (lb-in) | 14.39 | 16.44 | 14.8 | 17.1 | 19.82 | 20.67 | 19.56 | 17.12 | 19.34 | 17.21 | | |
| $M_H$ (Nm) | 1.61 | 1.86 | 1.67 | 1.93 | 2.24 | 2.34 | 2.21 | 1.93 | 2.19 | 1.94 | 4.7 | 4.4 |
| $t_s1$ (min) | 3.12 | 2.8 | 0.85 | 0.66 | 0.72 | 0.97 | 0.76 | 0.66 | 0.56 | 0.53 | 4.5 | 2.8 |
| $t_s2$ (min) | 4.54 | 4.15 | 1.29 | 0.93 | 1.03 | 1.56 | 1.11 | 0.95 | 0.71 | 0.67 | | |
| $t_c90$ | 25.08 | 26.31 | 21.4 | 16.1 | 17.74 | 30.64 | 17.89 | 11.12 | 14.44 | 10.6 | 43.5 | 26 |
| Mold cure cond. (min/° C.) | 30/177 | 30/177 | 20/160 | 16/160 | 17/160 | 30/160 | 18/160 | 12/160 | 12/177 | 8/177 | | |
| Post cure cond. (h/° C./atm) | 8/288/air | 8/288/air | 16/288/$N_2$ | 16/288/$N_2$ | 16/288/$N_2$ | 16/288/$N_2$ | 16/288/$N_2$ | 16/288/$N_2$ | 16/288/$N_2$ | 16/288/$N_2$ | | |
| $T_b$ (psi) | 1885 | 2169 | 1947 | 1219 | 1970 | 1990 | 1867 | 1877 | 1927 | 1701 | | |
| $T_b$ (MPa) | 13 | 14.95 | 13.42 | 8.4 | 13.58 | 13.72 | 12.87 | 12.94 | 13.28 | 11.73 | 13.4 | 14.2 |
| $E_b$ (%) | 197 | 171 | 179 | 105 | 162 | 145 | 148 | 149 | 151 | 144 | 165 | 145 |
| $M_{100}$ (psi) | 621 | 827 | 619 | 1056 | 884 | 1005 | 919 | 982 | 963 | 895 | | |
| $M_{100}$ (MPa) | 4.28 | 5.7 | 4.27 | 7.28 | 6.09 | 6.93 | 6.34 | 6.77 | 6.64 | 6.17 | 7.4 | 9.1 |
| 204° C., 70 h, 25% deflection (%) | 29 | 20 | 23 | | 13 | 9.2 | 10 | 11 | 16 | | | |
| 230° C., 70 h (%) | | | | | | | | | | | 16 | 14 |

βCure characteristics (MDR, 1 h @ 177° C.)

TABLE 5

| | Sample | | | | | | |
|---|---|---|---|---|---|---|---|
| | 13 | 14 | 15 | 16 | 17 | 18 | 19 |
| Perfluorosebacamidine | 0.7 | 1. | 1.25 | 1.5 | | | |
| Perfluorooctanamidine | | | | | 1 | 2 | 3 |
| $M_L$ (lb-in) | 0.74 | 1.52 | 1.83 | 2.22 | 0.47 | 0.73 | 0.84 |
| $M_L$ (Nm) | 0.08 | 0.17 | 0.21 | 0.25 | 0.05 | 0.08 | 0.09 |
| $M_H$ (lb-in) | 7.33 | 9.21 | 10.32 | 11.63 | 5.88 | 8.71 | 9.97 |
| $M_H$ (Nm) | 0.83 | 1.04 | 1.17 | 1.31 | 0.66 | 0.98 | 1.13 |
| $t_s2$ (min) | 1.46 | 0.72 | 0.61 | 0.47 | 1.1 | 0.69 | 0.6 |
| $t_C90$ (min) | 14.23 | 14.12 | 14.57 | 12.88 | 11.02 | 9.44 | 10.21 |
| mold cure cond. (min/° C.) | 30/177 | 30/177 | 30/177 | 30/177 | 15/177 | 15/177 | 15/177 |
| post cure cond. (h/° C./atm) | G | 8/288/$N_2$ | 8/288/$N_2$ | G | 8/288/$N_2$ | 8/288/$N_2$ | 8/288/$N_2$ |
| $T_b$ (psi) | 1242 | 1306 | 1410 | 1524 | 962 | 1289 | 1521 |
| $T_b$ (MPa) | 8.56 | 9 | 9.72 | 10.51 | 6.63 | 8.89 | 10.49 |
| $E_b$ 100% | 247 | 191 | 168 | 106 | 328 | 212 | 167 |
| $M_{100}$ (psi) | 357 | 406 | 498 | 1374 | 270 | 379 | 597 |
| $M_{100}$ (MPa) | 2.46 | 2.8 | 3.43 | 9.47 | 1.86 | 2.61 | 4.12 |
| 204° C., 70 h (%) | 11 | 17 | 19 | 11 | 63 | 40 | 24 |

TABLE 6

| | Sample | | | | | | | | | | |
|---|---|---|---|---|---|---|---|---|---|---|---|
| | 20* | 21 | 22 | 23 | 24 | 25 | 26 | 27 | 28 | 29 | 30 |
| Polymer A | 100 | 100 | 100 | 100 | 100 | 100 | | 100 | 100 | 100 | |
| Polymer B | | | | | | | 100 | | | | |
| Polymer D | | | | | | | | | | | 100 |
| Carbon Black N990 | 25 | 25 | 25 | 25 | 25 | 25 | 25 | 25 | 25 | 25 | 25 |
| Fluorogard PCA | 1.5 | 1.5 | 1.5 | 1.5 | 1.5 | 1.5 | 1.5 | | | | |
| BOAP | 1 | 0.5 | 1 | 1 | 1 | 1 | 1 | 1.5 | 2 | 1.5 | 1.5 |
| Perfluorosuberamidine | | 0.5 | 0.5 | | | | | | | | |
| Perfluorosebacamidine | | | | 0.25 | 0.75 | | | | | | |
| Perfluorooctanamidine | | | | | | 1 | 1 | 1.25 | 1.25 | | |
| Perfluoroheptanamidine | | | | | | | | | | 1.25 | 1.25 |

*Comparative Sample

TABLE 7

| | Sample | | | | | | | | | | |
|---|---|---|---|---|---|---|---|---|---|---|---|
| | 20* | 21 | 22 | 23 | 24 | 25 | 26 | 27 | 28 | 29 | 30 |
| $M_L$ (lb-in) | | 0.39 | 0.95 | 0.46 | 1.4 | 0.33 | 0.72 | 0.47 | 0.36 | 0.72 | 1.61 |
| $M_L$ (Nm) | | 0.04 | 0.11 | 0.05 | 0.16 | 0.04 | 0.08 | 0.05 | 0.04 | 0.08 | 0.18 |
| $M_H$ (lb-in) | | 0.99 | 18 | 12.14 | 17.3 | 13.7 | 18.9 | 16 | 16.07 | 15.87 | 18.65 |
| $M_H$ (Nm) | | 0.11 | 2.03 | 1.37 | 1.95 | 1.55 | 2.14 | 1.81 | 1.82 | 1.79 | 2.11 |
| $t_s2$ (min) | 5.9 | 2.17 | 0.96 | 3.09 | 0.76 | 1.29 | 0.84 | 1.29 | 1.37 | 0.93 | 0.66 |
| $t_C90$ (min) | 21.3 | 20.9 | 15 | 25 | 17.1 | 18.41 | 18.33 | 16.3 | 16.05 | 12.68 | 7.28 |
| Mold cure cond. (min/° C.) | 30/177 | 30/177 | 30/177 | 30/177 | 30/177 | 20/177 | 20/177 | 15/177 | 15/177 | 15/177 | 15/177 |
| post cure cond (h/° C./atm) | G | 8/288/air | | 16/233/$N_2$ | 8/288/$N_2$ | 8/288/air | 8/288/air | 16/288/$N_2$ | 16/288/$N_2$ | 16/288/$N_2$ | 16/288/$N_2$ |
| $T_b$ (psi) | 2073 | 1354 | 1976 | 1659 | 1382 | 1878 | 1669 | 2158 | 1924 | 2009 | 2385 |
| $T_b$ (MPa) | 14.29 | 9.33 | 13.62 | 11.44 | 9.53 | 12.95 | 11.51 | 14.88 | 13.26 | 13.85 | 16.44 |
| $E_b$ (%) | 136 | 243 | 135 | 190 | 138 | 195 | 143 | 169 | 142 | 166 | 143 |
| $M_{100}$ (Psi) | 1180 | 348 | 1211 | 502 | 750 | 589 | 800 | 933 | 960 | | |
| $M_{100}$ (MPa) | 8.13 | 2.4 | 8.35 | 3.46 | 5.17 | 4.06 | 5.52 | 6.43 | 6.62 | 0.01 | 0.01 |
| 204° C., 70 h, 18% def. (%) | | | | | | | | | 14 | | |
| 204° C., 70 h, 25% def. (%) | | | | | | 27 | 9 | 17 | | | |
| 230° C., 70 h (%) | 21 | 31 | 17 | 31 | 20 | | | | | | |
| 260, 70 h, 18% def. (%) | | | | | | | | | | 19 | 19 |

As can be seen from the data, the novel curatives of the Example provide comparable physical properties to standard use of BOAP, but due to the low melting points and higher compatibility of the Curatives A and B and the fast acting amidine curatives and accelerators, the curatives and accelerators of the invention provide faster, more reliable curing of the perfluoropolymer to form the perfluoroelastomer.

EXAMPLE 6

Further Samples were prepared using polymers having the same monomers as used in Example 5, however, the polymers in this Example were mixtures of two different molecular weight chains Polymer B noted above in Example 5. The formulations are shown in Table 8 below. The polymers were polymerized in the same manner and Mooney viscosity was measured at 100° C. on a TechPro® viscTECH TPD-1585 viscometer. To the polymers noted above, used in these compositions, were added heptafluorobutyrylamidine as a curative and as a cure accelerator. The heptafluorobutyrylamidine was obtained from SynQuest Laboratories, Inc., Alachua, Fla. All other components are as described above in Example 5.

Test specimens were made by mixing a tetrapolymer and the curatives to form a perfluoroelastomeric composition, and adding carbon black to that composition, using a Brabender internal mixer. The compounds, upon mixing, were shaped into O-ring preforms, molded to cure the performs into seals and then postcured into Size 214 O-rings in accordance with the cure and postcure conditions noted in Table 9 below. The rings were tested for tensile properties using ASTM-D-412, Method B, and the following parameters were recorded: TB (tensile at break in MPa); $E_B$ (elongation at break in %); and $M_{100}$ (modulus at 100% elongation in MPa). Compression set of O-ring samples was determined in accordance with ASTM-D-395, Method B. Cure characteristics were measured using a Monsanto MDR 2000 under the following conditions:

Moving die frequency: 1.6667 Hz
Oscillation amplitude: 0.5 deg arc
Temperature: as indicated in Tables herein
Sample size: disks of 1.6 inch diameter, thickness of 0.17 inch and 9.5 g weight
Duration of test: 60 minutes Table 9 includes the data directed to the effect of the monoamidine noted as a curative for a perfluoroelastomeric composition and as a cure accelerator for a BOAP-containing perfluoroelastomeric composition. In Samples Nos. 31-34, the Polymer B compositions each included 100 phr of polymer and 25 phr Carbon Black N990 and BOAP as noted in Table 8 which were cured and/or accelerated with the amidine as indicated. The information in Table 8 are indicated in parts per hundred. Sample 31 represents the control. In Table 9, in compression set data, the percentage measurement indicates percentage deflection and the physical property data is based on post cured samples. The data demonstrate the curative and acceleration affect of the amidine cure accelerators of the invention.

TABLE 8

| | Sample | | | |
|---|---|---|---|---|
| | 31* | 32 | 33 | 34 |
| Polymer B (110 Mooney Viscosity) | | | | 75 |
| Polymer B (24 Mooney Viscosity) | 25 | 25 | 25 | 25 |
| Polymer B (114 Mooney Viscosity) | 75 | 75 | 75 | |
| Carbon Black N990 | 25 | 25 | 25 | 25 |
| Heptafluorobutyrylamidine | | 1.54 | 0.64 | 0.64 |
| BOAP | 1.5 | | 1.5 | |

*Control

TABLE 9

| | Sample | | | |
|---|---|---|---|---|
| | 31* | 32 | 33 | 34 |
| meq amidine/100 g polymer | 0 | 7.26 | 3.03 | 3.03 |
| $M_L$ (lb-in) | 0.80 | 3.05 | 1.65 | 1.22 |
| $M_H$ (lb-in) | 15.85 | 13.97 | 16.76 | 8.76 |
| $t_s2$ (min) | 5.68 | 0.50 | 0.69 | 0.76 |
| $t_c90$ | 25.94 | 4.08 | 11.23 | 6.02 |
| Mold cure cond. (min/° C.) | 30/177 | 15/177 | 15/177 | 15/177 |
| Post cure cond. (h/° C./atm) | 24/288/$N_2$ | 24/288/$N_2$ | 24/288/$N_2$ | 24/288/$N_2$ |
| $T_b$ (psi) | 3171 | 2003 | 2375 | 1756 |
| $E_b$(%) | 122 | 121 | 117 | 225 |
| $M_{100}$ (psi) | 2393 | 1427 | 1924 | 625$^£$ |
| Hardness Durometer M | 84 | 78 | 84 | 78 |
| Compression Set 204° C./70 h/18% | 10.00 | 7.69 | 12.00 | 32.00 |
| Compression Set 204° C./70 h/25% | 9.99 | 8.33 | 8.57 | 28.57 |
| Compression Set 230° C./70 h/18% | 12.00 | 3.84 | 8.00 | 36.00 |
| Compression Set 230° C./70 h/25% | 11.42 | 8.33 | 8.57 | 34.28 |

*Control

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A cure accelerator for perfluoroelastomeric compositions having formula (I):

wherein Y is selected from the group consisting of substituted alkyl, alkoxy, aryl, aralkyl or aralkoxy groups of from 1 to about 22 carbon atoms; substituted or unsubstituted halogenated alkyl, alkoxy, aryl, aralkyl or aralkoxy groups of from about 1 to about 22 carbon atoms; and perfluoroalkyl, perfluoroalkoxy, perfluoroaryl, perfluoroaralkyl or perfluoroaralkoxy groups of from 1 to about 22 carbon atoms; and $R^1$ is hydrogen; substituted or unsubstituted lower alkyl or alkoxy groups of from 1 to about 6 carbon atoms; and an amino group; and $R^2$ is $R^1$ or hydroxyl, wherein the cure accelerator is capable of accelerating the curing of a curable perfluoroelastomeric composition comprising a curable perfluoropolymer and a diphenyl-based curative and upon cure the crosslinks formed are substantially free of amidine moieties and wherein the cure accelerator is present in the perfluoroelastomeric composition in an amount of about 0.1 to about 5 parts by weight of the cure accelerator per 100 parts by weight of the curable perfluoropolymer in the perfluoroelastomeric composition.

2. The cure accelerator according to claim 1, wherein Y is a perfluorinated alkyl group having about 1 to about 9 carbon atoms.

3. The cure accelerator according to claim 1, wherein the cure accelerator is selected from the group consisting of perfluorooctanamidine, heptafluorobutyrylamidine, trifluoromethylbenzamidoxime, trifluoromethoxylbenzamidoxime, and combinations thereof.

4. The cure accelerator according to claim 1, wherein the cure accelerator is capable of accelerating the cure of perfluoroelastomeric compositions comprising at least one cyano curesite monomer.

5. The cure accelerator according to claim 1, wherein the cure accelerator is capable of accelerating the cure of perfluoroelastomeric compositions comprising bisaminophenol and its derivatives.

6. The cure accelerator according to claim 1, wherein Y is selected from the group consisting of perfluoroalkyl, perfluoroalkoxy, substituted aryl groups and substituted and unsubstituted halogenated aryl groups.

7. The cure accelerator according to claim 1, wherein the curative is capable of curing perfluoroelastomeric compositions comprising at least one cyano curesite monomer.

8. The cure accelerator according to claim 1, wherein $R^2$ is hydroxyl, hydrogen or a substituted or unsubstituted alkyl group of from 1 to about 6 carbon atoms.

9. The cure accelerator according to claim 8, wherein $R^2$ is hydroxyl or hydrogen.

10. The cure accelerator according to claim 1, wherein $R^1$ is hydrogen or a substituted or unsubstituted lower alkyl group of from 1 to about 6 carbon atoms and $R^2$ is hydroxyl or hydrogen.

11. The cure accelerator according to claim 10, wherein $R^1$ is hydrogen.

12. The cure accelerator according to claim 1, wherein the curative is a perfluoroalkylamidine.

13. The cure accelerator according to claim 1, wherein the curative is an arylamidine.

14. The cure accelerator according to claim 1, wherein the curative is an arylamidoxime.

15. A curable perfluoroelastomeric composition, comprising:
(a) a perfluoropolymer having at least one curesite monomer comprising a cyano functional group;
(b) a functionalized diphenyl-based curative; and
(c) about 0.1 to about 5 parts by weight per 100 parts by weight of the perfluoropolymer of a cure accelerator selected from the group consisting of at least one monoamidine-based cure accelerator, at least one monoamidoxime-based cure accelerator, at least one bisamidine-based cure accelerator and combinations thereof wherein upon cure of the composition the crosslinks formed are substantially free of amidine moieties.

16. The curable perfluoroelastomeric composition according to claim 15, wherein the perfluoropolymer is a perfluoropolymer that is a tetrapolymer of tetrafluoroethylene, perfluoroalkylvinylether, a primary cyano curesite monomer and a secondary cyano curesite monomer.

17. The curable perfluoroelastomeric composition according to claim 15, wherein the diphenyl-based curative has a sufficiently high molecular weight so that the melting point is no greater than about 240° C.

18. The curable perfluoroelastomeric composition according to claim 17, wherein the melting point is no greater than about 230° C.

19. The curable perfluoroelastomeric composition according to claim 18, wherein the melting point is no greater than about 225° C.

20. A curable perfluoroelastomeric composition, comprising:
(a) a perfluoropolymer having at least one curesite monomer comprising a cyano functional group;
(b) a functionalized diphenyl-based curative; and
(c) a cure accelerator selected from the group consisting of at least one monoamidine-based cure accelerator, at least one monoamidoxime-based cure accelerator, at least one bisamidine-based cure accelerator and combinations thereof, wherein the functionalized diphenyl-based curative has formula (III):

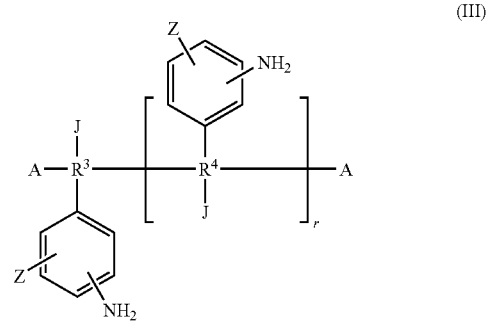

(III)

wherein r is 0 or 1;
$R^3$ and $R^4$ are each independently selected from the group consisting of a carbon atom; substituted and unsubstituted and branched and straight chain carbon groups of from about 2 to about 22 carbon atoms selected from the group consisting of alkyl groups, halogenated alkyl groups, and perfluorinated alkyl groups, each of which groups may be interrupted by at least one oxygen atom;
each Z is independently selected from the group consisting of an amino, mercapto, sulfhydryl, or hydroxyl group;
each J is independently selected to be formula (IV):

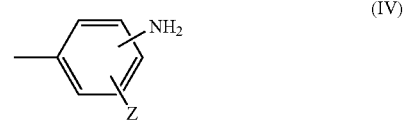

(IV)

or A; and
each A is independently selected from the group consisting of formula (IV); a fluorine atom; and unsubstituted and substituted and branched and straight chain carbon-based groups which are selected from the group consisting of alkyl, halogenated alkyl, and perfluoroalkyl groups of from 1 to about 22 carbon atoms; each of which groups may be interrupted by at least one oxygen atom; wherein when r is 0 and $R^3$ is a carbon atom, at least one of J and each A is not formula (IV), and wherein upon cure of the composition the crosslinks are substantially free of amidine moieties.

* * * * *